(12) United States Patent
Kaminski et al.

(10) Patent No.: US 9,523,084 B2
(45) Date of Patent: Dec. 20, 2016

(54) PHOSPHODEOXYRIBOSYL TRANSFERASE MUTANT ENZYMES AND USES THEREOF

(71) Applicant: Centre National De La Recherche Scientifique, Paris (FR)

(72) Inventors: Pierre-Alexandre Kaminski, Paris (FR); Gilles Labesse, Montpellier (FR)

(73) Assignee: Centre National De La Recherche Scientifique (CNRS) (FR)

( * ) Notice: Subject to any disclaimer, the term of this patent is extended or adjusted under 35 U.S.C. 154(b) by 0 days.

(21) Appl. No.: 14/441,560

(22) PCT Filed: Nov. 8, 2013

(86) PCT No.: PCT/EP2013/073441
§ 371 (c)(1),
(2) Date: May 8, 2015

(87) PCT Pub. No.: WO2014/072487
PCT Pub. Date: May 15, 2014

(65) Prior Publication Data
US 2015/0267181 A1  Sep. 24, 2015

(30) Foreign Application Priority Data
Nov. 8, 2012  (EP) ..................... 12306377

(51) Int. Cl.
*C12N 9/10* (2006.01)
*C12N 9/24* (2006.01)

(52) U.S. Cl.
CPC .......... *C12N 9/1077* (2013.01); *C12N 9/2497* (2013.01); *C12Y 204/02006* (2013.01)

(58) Field of Classification Search
None
See application file for complete search history.

(56) References Cited

U.S. PATENT DOCUMENTS

| | | | |
|---|---|---|---|
| 4,873,191 A | 10/1989 | Wagner et al. | |
| 2014/0249204 A1 | 9/2014 | Vainchenker et al. | |

FOREIGN PATENT DOCUMENTS

| | | | |
|---|---|---|---|
| EP | 1692281 A1 | 8/2006 | |
| EP | 1692281 B1 | 12/2007 | |
| EP | 1692281 B8 | 2/2008 | |
| WO | 98/10088 A1 | 3/1998 | |
| WO | 0114566 A2 | 3/2001 | |
| WO | WO 01/14566 | * 3/2001 | |
| WO | 2004020602 A2 | 3/2004 | |

OTHER PUBLICATIONS

Ali et al. "Incorporation of an inducible nucleotide analog into DNA by DNA polymerases" Bioorganic & Medicinal chemistry, 2009, 17, 7, 2859-2863.
Bao et al. "Total biosynthesis of deoxynucleoside triphosphates using deoxynucleoside monophosphate kinases for PCR application" Biotechnol Bioeng, 2007, 98, 1-11.
Brinster et al. "Regulation of metallothionein-thymidine kinase fusion plasmids injected into mouse eggs" Nature, 1982, 296:39-42.
Burgess et al. "Syntheses of nucleoside triphosphates" Chem Rev, 2000, 100, 2047-2060.
Caton-Williams et al. "Protection-free one-pot synthesis of 2'-deoxynucleoside 5'-triphosphates and DNA polymerization" Org Lett, 2011, 13, 4156-4159.
Doddapaneni et al. "RCL hydrolyzes 2'-deoxyribonucleoside 5'-monophosphate via formation of a reaction intermediate" Biochemistry 50, 4712-4719.
Eriksson et al. "Structure and function of cellular deoxyribonucleoside kinases" Cell Mol Life Sci, 2002, 59, 1327-1346.
Freeman et al. "2-amino-9-(3-azido-2,3-dideoxy-beta-D-erythro-pentofuranosyl)-6-substitute d-9H-purines: synthesis and anti-HIV activity" Bioorg Med Chem, 1995, 03, 447-458.
Gerlt et al. "Enzyme (re)design: lessons from natural evolution and computation" Curr Opin Chem Biol, 2009, 13, 10-18.
Gibson et al. "Creation of a bacterial cell controlled by a chemically synthesized genome" Science, 2010, 329, 52-56.
Gibson et al. "Chemical synthesis of the mouse mitochondrial genome" Nat Methods, 2010, 7, 901-903.
Ghiorghi et al. "The c-Myc target gene Rcl (C6orf108) encodes a novel enzyme, deoxynucleoside 5'- monophosphate N-glycosidase" J Biol Chem 2007, 282, 8150-8156.
Hebrard et al. "Development of gene therapy in association with clinically used cytotoxic deoxynucleoside analogues" Cancer Gene Therapy 2009, 16, 541-550.
Johnson et al. "Overview of the synthesis of nucleoside phosphates and polyphosphates" Curr Protoc Nucleic Acid Chem, 2004, Chapter 13, Unit 13 11.
Kaminski "Functional cloning, heterologous expression, and purification of two different N-deoxyribosyltransferases from Lactobacillus helveticus" J Biol Chem, 2002, 277, 14400-14407.
Kaminski et al. "In vivo reshaping the catalytic site of nucleoside 2'-deoxyribosyltransferase for dideoxy- and didehydronucleosides via a single amino acid substitution" J Biol Chem, 2008, 283, 20053-20059.
Khakshoor et al. "Chemistry of nucleic acids: impacts in multiple fields" Chem Commun, 2011, 47, 7018-7024.
Kilstrup et al "Nucleotide metabolism and its control in lactic acid bacteria" Diversity and applications of bacillus basteriocins, 2005, 29, 3, 555-590.
Ladner et al. "Enzymatic-Synthesis of Deoxy-Atp Using DNA as Starting Material" J Org Chem, 1985, 50, 1076-1079.
Mikhailopulo et al. "Biologically important nucleosides: modern trends in biotechnology and application" Mendeleev Commun, 2011, 21, 57-6.
Miller et al. "Improved retroviral vectors for gene transfer and expression" BioTechniques, 1989, 7:980-990, 1992.

(Continued)

*Primary Examiner* — Christian Fronda
(74) *Attorney, Agent, or Firm* — Banner & Witcoff, Ltd.

(57) ABSTRACT

The present invention relates to enzyme mutants obtained from the nucleoside deoxyribosyltransferase (NDT) of *Lactobacilli* bacteria. These mutants are surprisingly able to exchange deoxyribose mono-, bi- and triphosphate between various nucleobases. In vitro syntheses have been successfully performed with several nucleobase analogs. These enzyme mutants provide new tools to synthesize, in vitro and/or in vivo, dNTPs or analogs thereof.

24 Claims, 2 Drawing Sheets

(56) References Cited

OTHER PUBLICATIONS

Figure 1:
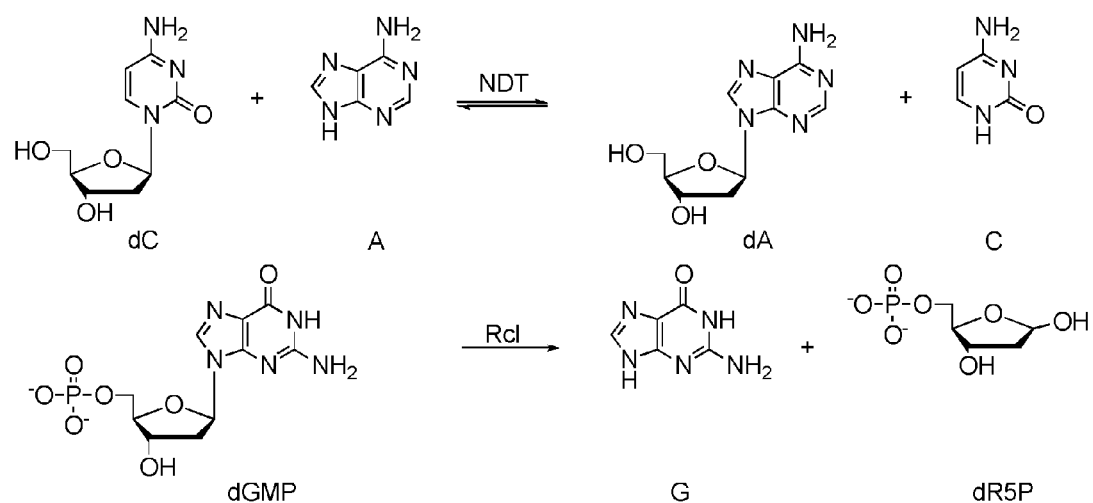

Miyamoto et al. "Characterization of N-deoxyribosyltransferase from *Lactococcus lactis* subsp" Lactis, Biochimica et Biophysica Acta—Proteins & Proteomics, 2007, 1774, 10, 1323-1330.

Munch-Peterson et al. "Four Deoxynucleoside Kinase Activities from *Drosophila melanogaster* are contained within a single monomeric enzyme, a new multifunctional deoxynucleoside kinase" J. Biol. Chem. 1998, vol. 273, No. 7.

Nordlund et al. "Ribonucleotide reductases" Annu Rev Biochem, 2006, 75, 681-706.

Porter et al. "Identification of the active site nucleophile in nucleoside 2-deoxyribosyltransferase as glutamic acid 98" J Biol Chem, 1995, 270, 15551-15556.

Warren "Modified bases in bacteriophage DNAs" Annu Rev Microbiol, 1980, 34, 137-158.

Yang et al. "Structural characterization of the mammalian deoxynucleotide N-hydrolase Rcl and its stabilizing interactions with two inhibitors" J Mol Biol, 2009, 394, 435-447.

* cited by examiner

SEQUENCE LISTING

```
<160> NUMBER OF SEQ ID NOS: 49

<210> SEQ ID NO 1
<211> LENGTH: 157
<212> TYPE: PRT
<213> ORGANISM: Lactobacillus leichmannii

<400> SEQUENCE: 1

Met Pro Lys Lys Thr Ile Tyr Phe Gly Ala Gly Trp Phe Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Asp Val Gly Leu Gly
                85                  90                  95

Met Glu Leu Gly Tyr Ala Leu Ser Gln Gly Lys Tyr Val Leu Leu Val
                100                 105                 110

Ile Pro Asp Glu Asp Tyr Gly Lys Pro Ile Asn Leu Met Ser Trp Gly
            115                 120                 125

Val Ser Asp Asn Val Ile Lys Met Ser Gln Leu Lys Asp Phe Asn Phe
        130                 135                 140

Asn Lys Pro Arg Phe Asp Phe Tyr Glu Gly Ala Val Tyr
145                 150                 155
```

```
<210> SEQ ID NO 2
<211> LENGTH: 163
<212> TYPE: PRT
<213> ORGANISM: Rattus norvegicus

<400> SEQUENCE: 2

Met Ala Ala Ser Gly Glu Gln Ala Pro Cys Ser Val Tyr Phe Cys Gly
1               5                   10                  15

Ser Ile Arg Gly Gly Arg Glu Asp Gln Ala Leu Tyr Ala Arg Ile Val
            20                  25                  30

Ser Arg Leu Arg Arg Tyr Gly Lys Val Leu Thr Glu His Val Ala Asp
        35                  40                  45

Ala Glu Leu Glu Pro Leu Gly Glu Ala Ala Gly Gly Asp Gln Phe
    50                  55                  60

Ile His Glu Gln Asp Leu Asn Trp Leu Gln Gln Ala Asp Val Val Val
65                  70                  75                  80

Ala Glu Val Thr Gln Pro Ser Leu Gly Val Gly Tyr Glu Leu Gly Arg
                85                  90                  95

Ala Val Ala Leu Gly Lys Pro Ile Leu Cys Leu Phe Arg Pro Gln Ser
                100                 105                 110

Gly Arg Val Leu Ser Ala Met Ile Arg Gly Ala Ala Asp Gly Ser Arg
            115                 120                 125

Phe Gln Val Trp Asp Tyr Ala Glu Gly Glu Val Glu Thr Met Leu Asp
    130                 135                 140

Arg Tyr Phe Glu Ala Tyr Leu Pro Gln Lys Thr Ala Ser Ser Ser His
145                 150                 155                 160

Pro Ser Ala

<210> SEQ ID NO 3
<211> LENGTH: 157
<212> TYPE: PRT
<213> ORGANISM: artificial
<220> FEATURE:
<223> OTHER INFORMATION: PDTM1 enzyme mutant

<400> SEQUENCE: 3

Met Pro Lys Lys Thr Ile Tyr Phe Gly Ala Gly Trp Phe Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Glu Ser Val Gly Leu Gly
                85                  90                  95

Met Glu Leu Gly Tyr Ala Leu Ser Gln Gly Lys Tyr Val Leu Leu Val
                100                 105                 110

Ile Pro Asp Glu Asp Tyr Gly Lys Pro Ile Asn Leu Met Ser Trp Gly
            115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Tyr
145                 150                 155
```

<210> SEQ ID NO 4
<211> LENGTH: 157
<212> TYPE: PRT
<213> ORGANISM: artificial
<220> FEATURE:
<223> OTHER INFORMATION: PDTM2 enzyme mutant

<400> SEQUENCE: 4

Met Pro Lys Lys Thr Ile Tyr Phe Gly Ala Gly Trp Phe Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Ser Val Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Tyr
145                 150                 155

<210> SEQ ID NO 5
<211> LENGTH: 157
<212> TYPE: PRT
<213> ORGANISM: artificial
<220> FEATURE:
<223> OTHER INFORMATION: PDTM3 enzyme mutant

<400> SEQUENCE: 5

Met Pro Lys Lys Thr Ile Tyr Phe Gly Ala Gly Trp Arg Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Glu Ser Val Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Asn Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Tyr
145                 150                 155

```
<210> SEQ ID NO 6
<211> LENGTH: 157
<212> TYPE: PRT
<213> ORGANISM: artificial
<220> FEATURE:
<223> OTHER INFORMATION: PDTM4 enzyme mutant

<400> SEQUENCE: 6

Met Pro Lys Lys Thr Ile Tyr Phe Gly Ala Gly Trp Arg Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Ser Val Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Tyr
145                 150                 155

<210> SEQ ID NO 7
<211> LENGTH: 157
<212> TYPE: PRT
<213> ORGANISM: artificial
<220> FEATURE:
<223> OTHER INFORMATION: PDTM5 enzyme mutant

<400> SEQUENCE: 7

Met Pro Lys Lys Thr Ile Tyr Phe Gly Ala Gly Trp Gln Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Ser Val Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Tyr
145                 150                 155
```

```
<210> SEQ ID NO 8
<211> LENGTH: 157
<212> TYPE: PRT
<213> ORGANISM: artificial
<220> FEATURE:
<223> OTHER INFORMATION: PDTT0 enzyme mutant

<400> SEQUENCE: 8

Met Pro Lys Lys Thr Ile Tyr Phe Gly Ala Gly Trp Arg Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Gly Thr Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Tyr
145                 150                 155

<210> SEQ ID NO 9
<211> LENGTH: 157
<212> TYPE: PRT
<213> ORGANISM: artificial
<220> FEATURE:
<223> OTHER INFORMATION: PDTT1 enzyme mutant

<400> SEQUENCE: 9

Met Pro Lys Lys Thr Ile Tyr Phe Gly Ala Gly Trp Arg Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Gly Thr Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Lys
145                 150                 155
```

<210> SEQ ID NO 10
<211> LENGTH: 157
<212> TYPE: PRT
<213> ORGANISM: artificial
<220> FEATURE:
<223> OTHER INFORMATION: PDTT2 enzyme mutant

<400> SEQUENCE: 10

Met Pro Lys Lys Thr Ile Tyr Phe Gly Ala Gly Trp Arg Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Gln Gly Thr Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Tyr
145                 150                 155

<210> SEQ ID NO 11
<211> LENGTH: 34
<212> TYPE: DNA
<213> ORGANISM: artificial
<220> FEATURE:
<223> OTHER INFORMATION: primer F13R

<400> SEQUENCE: 11
cttcggtgcc ggctggcgca ctgaccgcca aaac                         34

<210> SEQ ID NO 12
<211> LENGTH: 35
<212> TYPE: DNA
<213> ORGANISM: artificial
<220> FEATURE:
<223> OTHER INFORMATION: primer F13Q

<400> SEQUENCE: 12
cttcggtgcc ggctggcaga ctgaccgcca aaaca                        35

<210> SEQ ID NO 13
<211> LENGTH: 35
<212> TYPE: DNA
<213> ORGANISM: artificial
<220> FEATURE:
<223> OTHER INFORMATION: primer F13Qbis

<400> SEQUENCE: 13
tgttttggcg gtcagtctgc cagccggcac cgaag                        35

<210> SEQ ID NO 14
<211> LENGTH: 33
<212> TYPE: DNA

```
<213> ORGANISM: artificial
<220> FEATURE:
<223> OTHER INFORMATION: primer D92S

<400> SEQUENCE: 14
atccctgacg aagaaagcgt cggcctgggc atg                                      33

<210> SEQ ID NO 15
<211> LENGTH: 35
<212> TYPE: DNA
<213> ORGANISM: artificial
<220> FEATURE:
<223> OTHER INFORMATION: primer N123S

<400> SEQUENCE: 15
ctacggcaag ccgatcagcc tcatgagctg gggcg                                    35

<210> SEQ ID NO 16
<211> LENGTH: 35
<212> TYPE: DNA
<213> ORGANISM: artificial
<220> FEATURE:
<223> OTHER INFORMATION: primer N123Sbis

<400> SEQUENCE: 16
cgccccagct catgaggctg atcggcttgc cgtag                                    35

<210> SEQ ID NO 17
<211> LENGTH: 35
<212> TYPE: DNA
<213> ORGANISM: artificial
<220> FEATURE:
<223> OTHER INFORMATION: primer N123T

<400> SEQUENCE: 17
ctacggcaag ccgatcaccc tcatgagctg gggcg                                    35

<210> SEQ ID NO 18
<211> LENGTH: 35
<212> TYPE: DNA
<213> ORGANISM: artificial
<220> FEATURE:
<223> OTHER INFORMATION: primer N123Tbis

<400> SEQUENCE: 18
cgccccagct catgagggtg atcggcttgc cgtag                                    35

<210> SEQ ID NO 19
<211> LENGTH: 32
<212> TYPE: DNA
<213> ORGANISM: artificial
<220> FEATURE:
<223> OTHER INFORMATION: primer E91Q

<400> SEQUENCE: 19
tgtctacatc cctgacgaac agggcaccgg cc                                       32

<210> SEQ ID NO 20
<211> LENGTH: 32
<212> TYPE: DNA
<213> ORGANISM: artificial
<220> FEATURE:
<223> OTHER INFORMATION: primer E91Qbis

<400> SEQUENCE: 20
ggccggtgcc ctgttcgtca gggatgtaga ca                                       32
```

```
<210> SEQ ID NO 21
<211> LENGTH: 40
<212> TYPE: DNA
<213> ORGANISM: artificial
<220> FEATURE:
<223> OTHER INFORMATION: primer Y157K

<400> SEQUENCE: 21
gcaagctttt actttacggc accttcgtag aagtcgaagc                             40

<210> SEQ ID NO 22
<211> LENGTH: 37
<212> TYPE: DNA
<213> ORGANISM: artificial
<220> FEATURE:
<223> OTHER INFORMATION: primer G92T93

<400> SEQUENCE: 22
gtctacatcc ctgacgaaga aggcaccggc ctgggca                                37

<210> SEQ ID NO 23
<211> LENGTH: 37
<212> TYPE: DNA
<213> ORGANISM: artificial
<220> FEATURE:
<223> OTHER INFORMATION: primer G92T93 bis

<400> SEQUENCE: 23
tgcccaggcc ggtgccttct tcgtcaggga tgtagac                                37

<210> SEQ ID NO 24
<211> LENGTH: 471
<212> TYPE: DNA
<213> ORGANISM: artificial
<220> FEATURE:
<223> OTHER INFORMATION: DNA encoding PDTM1

<400> SEQUENCE: 24
atgccaaaaa agacgatcta cttcggtgcc ggctggttca ctgaccgcca aaacaaagcc       60
tacaaggaag ccatggaagc cctcaaggaa aacccaacga ttgacctgga aaacagctac      120
gttcccctgg acaaccagta caagggtatc cgggttgatg aacacccgga atacctgcat      180
gacaaggttt gggctacggc cacctacaac aacgacttga acgggatcaa gaccaacgac      240
atcatgctgg tgtctacat ccctgacgaa gaaagcgtcg gcctgggcat ggaactgggt       300
tacgccttga gccaaggcaa gtacgtcctt ttggtcatcc cggacgaaga ctacggcaag      360
ccgatcaacc tcatgagctg ggcgtcagc gacaacgtga tcaagatgag ccagctgaag       420
gacttcaact tcaacaagcc gcgcttcgac ttctacgaag gtgccgtata c              471

<210> SEQ ID NO 25
<211> LENGTH: 471
<212> TYPE: DNA
<213> ORGANISM: artificial
<220> FEATURE:
<223> OTHER INFORMATION: DNA encoding PDTM2

<400> SEQUENCE: 25
atgccaaaaa agacgatcta cttcggtgcc ggctggttca ctgaccgcca aaacaaagcc       60
tacaaggaag ccatggaagc cctcaaggaa aacccaacga ttgacctgga aaacagctac      120
gttcccctgg acaaccagta caagggtatc cgggttgatg aacacccgga atacctgcat      180
gacaaggttt gggctacggc cacctacaac aacgacttga acgggatcaa gaccaacgac      240
```

```
atcatgctgg gtgtctacat ccctgacgaa gaaagcgtcg gcctgggcat ggaactgggt    300
tacgccttga gccaaggcaa gtacgtcctt ttggtcatcc cggacgaaga ctacggcaag    360
ccgatcagcc tcatgagctg gggcgtcagc gacaacgtga tcaagatgag ccagctgaag    420
gacttcaact tcaacaagcc gcgcttcgac ttctacgaag gtgccgtata c             471
```

```
<210> SEQ ID NO 26
<211> LENGTH: 471
<212> TYPE: DNA
<213> ORGANISM: artificial
<220> FEATURE:
<223> OTHER INFORMATION: DNA encoding PDTM3

<400> SEQUENCE: 26
atgccaaaaa agacgatcta cttcggtgcc ggctggcgca ctgaccgcca aaacaaagcc     60
tacaaggaag ccatggaagc cctcaaggaa aacccaacga ttgacctgga aaacagctac    120
gttcccctgg acaaccagta caagggtatc cgggttgatg aacacccgga atacctgcat    180
gacaaggttt gggctacggc cacctacaac aacgacttga acgggatcaa gaccaacgac    240
atcatgctgg gtgtctacat ccctgacgaa gaaagcgtcg gcctgggcat ggaactgggt    300
tacgccttga gccaaggcaa gtacgtcctt ttggtcatcc cggacgaaga ctacggcaag    360
ccgatcaacc tcatgagctg gggcgtcagc gacaacgtga tcaagatgag ccagctgaag    420
gacttcaact tcaacaagcc gcgcttcgac ttctacgaag gtgccgtata c             471
```

```
<210> SEQ ID NO 27
<211> LENGTH: 471
<212> TYPE: DNA
<213> ORGANISM: artificial
<220> FEATURE:
<223> OTHER INFORMATION: DNA encoding PDTM4

<400> SEQUENCE: 27
atgccaaaaa agacgatcta cttcggtgcc ggctggcgca ctgaccgcca aaacaaagcc     60
tacaaggaag ccatggaagc cctcaaggaa aacccaacga ttgacctgga aaacagctac    120
gttcccctgg acaaccagta caagggtatc cgggttgatg aacacccgga atacctgcat    180
gacaaggttt gggctacggc cacctacaac aacgactTga acgggatcaa gaccaacgac    240
atcatgctgg gtgtctacat ccctgacgaa gaaagcgtcg gcctgggcat ggaactgggt    300
tacgccttga gccaaggcaa gtacgtcctt ttggtcatcc cggacgaaga ctacggcaag    360
ccgatcagcc tcatgagctg gggcgtcagc gacaacgtga tcaagatgag ccagctgaag    420
gacttcaact tcaacaagcc gcgcttcgac ttctacgaag gtgccgtata c             471
```

```
<210> SEQ ID NO 28
<211> LENGTH: 471
<212> TYPE: DNA
<213> ORGANISM: artificial
<220> FEATURE:
<223> OTHER INFORMATION: DNA encoding PDTM5

<400> SEQUENCE: 28
atgccaaaaa agacgatcta cttcggtgcc ggctggcaga ctgaccgcca aaacaaagcc     60
tacaaggaag ccatggaagc cctcaaggaa aacccaacga ttgacctgga aaacagctac    120
gttcccctgg acaaccagta caagggtatc cgggttgatg aacacccgga atacctgcat    180
gacaaggttt gggctacggc cacctacaac aacgacttga acgggatcaa gaccaacgac    240
atcatgctgg gtgtctacat ccctgacgaa gaaagcgtcg gcctgggcat ggaactgggt    300
```

```
tacgccttga gccaaggcaa gtacgtcctt ttggtcatcc cggacgaaga ctacggcaag      360
ccgatcagcc tcatgagctg gggcgtcagc gacaacgtga tcaagatgag ccagctgaag      420
gacttcaact tcaacaagcc gcgcttcgac ttctacgaag gtgccgtata c               471

<210> SEQ ID NO 29
<211> LENGTH: 471
<212> TYPE: DNA
<213> ORGANISM: artificial
<220> FEATURE:
<223> OTHER INFORMATION: DNA encoding PDTT0

<400> SEQUENCE: 29
atgccaaaaa agacgatcta cttcggtgcc ggctggcgca ctgaccgcca aaacaaagcc       60
tacaaggaag ccatggaagc cctcaaggaa aacccaacga ttgacctgga aaacagctac      120
gttcccctgg acaaccagta caagggtatc cgggttgatg aacacccgga ataccctgcat    180 gacaaggttt gggctacggc cacctacaac aacgacttga acgggatcaa gaccaacgac     240
atcatgctgg tgtctacat ccctgacgaa cagggcaccg gcctgggcat ggaactgggt     300
tacgccttga gccaaggcaa gtacgtcctt ttggtcatcc cggacgaaga ctacggcaag     360
ccgatcagcc tcatgagctg gggcgtcagc gacaacgtga tcaagatgag ccagctgaag    420
gacttcaact tcaacaagcc gcgcttcgac ttctacgaag gtgccgtata c               471

<210> SEQ ID NO 30
<211> LENGTH: 471
<212> TYPE: DNA
<213> ORGANISM: artificial
<220> FEATURE:
<223> OTHER INFORMATION: DNA encoding PDTT1

<400> SEQUENCE: 30
atgccaaaaa agacgatcta cttcggtgcc ggctggcgca ctgaccgcca aaacaaagcc       60
tacaaggaag ccatggaagc cctcaaggaa aacccaacga ttgacctgga aaacagctac      120
gttcccctgg acaaccagta caagggtatc cgggttgatg aacacccgga ataccctgcat    180 gacaaggttt gggctacggc cacctacaac aacgacttga acgggatcaa gaccaacgac     240
atcatgctgg tgtctacat ccctgacgaa gaaggcaccg gcctgggcat ggaactgggt     300
tacgccttga gccaaggcaa gtacgtcctt ttggtcatcc cggacgaaga ctacggcaag     360
ccgatcagcc tcatgagctg gggcgtcagc gacaacgtga tcaagatgag ccagctgaag    420
gacttcaact tcaacaagcc gcgcttcgac ttctacgaag gtgccgtaaa g              471

<210> SEQ ID NO 31
<211> LENGTH: 471
<212> TYPE: DNA
<213> ORGANISM: artificial
<220> FEATURE:
<223> OTHER INFORMATION: DNA encoding PDTT2

<400> SEQUENCE: 31
atgccaaaaa agacgatcta cttcggtgcc ggctggcgca ctgaccgcca aaacaaagcc       60
tacaaggaag ccatggaagc cctcaaggaa aacccaacga ttgacctgga aaacagctac      120
gttcccctgg acaaccagta caagggtatc cgggttgatg aacacccgga ataccctgcat    180 gacaaggttt gggctacggc cacctacaac aacgacttga acgggatcaa gaccaacgac     240
atcatgctgg tgtctacat ccctgacgaa cagggcaccg gcacgggcat ggaactgggt     300
tacgccttga gccaaggcaa gtacgtcctt ttggtcatcc cggacgaaga ctacggcaag     360
```

```
ccgatcagcc tcatgagctg gggcgtcagc gacaacgtga tcaagatgag ccagctgaag    420
gacttcaact tcaacaagcc gcgcttcgac ttctacgaag gtgccgtata c             471

<210> SEQ ID NO 32
<211> LENGTH: 5748
<212> TYPE: DNA
<213> ORGANISM: artificial
<220> FEATURE:
<223> OTHER INFORMATION: DNA of plasmid pET24a NDT

<400> SEQUENCE: 32
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcgggggc tcccttagg     180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta agggatttt gccgatttc ggcctattgg ttaaaaaatg agctgattta     420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaattat     600 tcatatcagg attatcaata ccatatttt gaaaaagccg tttctgtaat gaaggagaaa    660
actcaccgag gcagttccat aggatggcaa gatcctggta cggtctgcg attccgactc    720 gtccaacatc aatacaacct attaattcc cctcgtcaaa ataaggtta tcaagtgaga    780 aatcaccatg agtgacgact gaatccggtg agaatggcaa aagtttatgc atttcttcc    840 agacttgttc aacaggccag ccattacgct cgtcatcaaa atcactcgca tcaaccaaac    900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa atcccttaa   1440 cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
```

```
ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160 tccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
```

```
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgccaaaa aagacgatct acttcggtgc    5100
cggctggttc actgaccgcc aaaacaaagc ctacaaggaa gccatggaag ccctcaagga    5160
aaacccaacg attgacctgg aaaacagcta cgttcccctg gacaaccagt acaagggtat    5220
ccgggttgat gaacacccgg aatacctgca tgacaaggtt tgggctacgg ccacctacaa    5280
caacgacttg aacgggatca agaccaacga catcatgctg ggtgtctaca tccctgacga    5340
agaagacgtc ggcctgggca tggaactggg ttacgccttg agccaaggca agtacgtcct    5400
tttggtcatc ccggacgaag actacggcaa gccgatcaac ctcatgagct ggggcgtcag    5460
cgacaacgtg atcaagatga gccagctgaa ggacttcaac ttcaacaagc gcgcttcga    5520 cttctacgaa ggtgccgtat actaaggatc cgaattcgag ctccgtcgac aagcttgcgg    5580
ccgcactcga gcaccaccac caccaccact gagatccggc tgctaacaaa gcccgaaagg    5640
aagctgagtt ggctgctgcc accgctgagc aataactagc ataacccctt ggggcctcta    5700
aacgggtctt gagggttttt ttgctgaaag gaggaactat atccggat              5748
```

<210> SEQ ID NO 33
<211> LENGTH: 29
<212> TYPE: DNA
<213> ORGANISM: artificial
<220> FEATURE:
<223> OTHER INFORMATION: sequence of primer T7 prom

<400> SEQUENCE: 33
cgcgaaatta atacgactca ctataggg                                      29

<210> SEQ ID NO 34
<211> LENGTH: 27
<212> TYPE: DNA
<213> ORGANISM: artificial
<220> FEATURE:
<223> OTHER INFORMATION: sequence of primer T7 term

<400> SEQUENCE: 34
ggggttatgc tagttattgc tcagcgg                                       27

<210> SEQ ID NO 35
<211> LENGTH: 157
<212> TYPE: PRT
<213> ORGANISM: artificial
<220> FEATURE:
<223> OTHER INFORMATION: amino acid sequence of PDTT1 ter
      (G92/S123/Q13/T93/K157)

<400> SEQUENCE: 35

Met Pro Lys Lys Thr Ile Tyr Phe Gly Ala Gly Trp Gln Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Glu Gly Thr Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Lys
145                 150                 155

<210> SEQ ID NO 36
<211> LENGTH: 157
<212> TYPE: PRT
<213> ORGANISM: artificial
<220> FEATURE:
<223> OTHER INFORMATION: amino acid sequence of PDTT1 quinques
      (S92/S123/Q13/K157/Q91)

<400> SEQUENCE: 36

Met Pro Lys Lys Thr Ile Tyr Phe Gly Ala Gly Trp Gln Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Gln Ser Val Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Lys
145                 150                 155

<210> SEQ ID NO 37
<211> LENGTH: 157
<212> TYPE: PRT
<213> ORGANISM: artificial

<220> FEATURE:
<223> OTHER INFORMATION: amino acid sequence of PDTT1 sexies
      (G92/S123/Q13/T93/K157/Q91)

<400> SEQUENCE: 37

Met Pro Lys Lys Thr Ile Tyr Phe Gly Ala Gly Trp Gln Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Gln Gly Thr Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Lys
145                 150                 155

<210> SEQ ID NO 38
<211> LENGTH: 157
<212> TYPE: PRT
<213> ORGANISM: artificial
<220> FEATURE:
<223> OTHER INFORMATION: amino acid sequence of PDTT3
      (G92/S123/R13/P93/K157/Q91)

<400> SEQUENCE: 38

Met Pro Lys Lys Thr Ile Tyr Phe Gly Ala Gly Trp Arg Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Gln Gly Pro Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Lys
145                 150                 155

```
<210> SEQ ID NO 39
<211> LENGTH: 157
<212> TYPE: PRT
<213> ORGANISM: artificial
<220> FEATURE:
<223> OTHER INFORMATION: amino acid sequence of PDTT3b
      (G92/S123/R13/G93/K157/Q91)

<400> SEQUENCE: 39

Met Pro Lys Lys Thr Ile Tyr Phe Gly Ala Gly Trp Arg Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Gln Gly Gly Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Lys
145                 150                 155

<210> SEQ ID NO 40
<211> LENGTH: 157
<212> TYPE: PRT
<213> ORGANISM: artificial
<220> FEATURE:
<223> OTHER INFORMATION: amino acid sequence of PDTT4
      (G92/S123/R13/S93/K157/Q91)

<400> SEQUENCE: 40

Met Pro Lys Lys Thr Ile Tyr Phe Gly Ala Gly Trp Arg Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Gln Gly Ser Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125
```

Val Ser Asp Asn Val Ile Lys Met Ser Gln Leu Lys Asp Phe Asn Phe
130                 135                 140

Asn Lys Pro Arg Phe Asp Phe Tyr Glu Gly Ala Val Lys
145                 150                 155

<210> SEQ ID NO 41
<211> LENGTH: 157
<212> TYPE: PRT
<213> ORGANISM: artificial
<220> FEATURE:
<223> OTHER INFORMATION: amino acid sequence of PDTT5
      (G92/S123/R13/P93/R157/Q91)

<400> SEQUENCE: 41

Met Pro Lys Lys Thr Ile Tyr Phe Gly Ala Gly Trp Arg Thr Asp Arg
1               5                   10                  15

Gln Asn Lys Ala Tyr Lys Glu Ala Met Glu Ala Leu Lys Glu Asn Pro
                20                  25                  30

Thr Ile Asp Leu Glu Asn Ser Tyr Val Pro Leu Asp Asn Gln Tyr Lys
            35                  40                  45

Gly Ile Arg Val Asp Glu His Pro Glu Tyr Leu His Asp Lys Val Trp
        50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Gln Gly Pro Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
130                 135                 140

Asn Lys Pro Arg Phe Asp Phe Tyr Glu Gly Ala Val Arg
145                 150                 155

<210> SEQ ID NO 42
<211> LENGTH: 157
<212> TYPE: PRT
<213> ORGANISM: artificial
<220> FEATURE:
<223> OTHER INFORMATION: amino acid sequence of PDTT7
      (G92/S123/R13/G93/R157/Q91)

<400> SEQUENCE: 42

Met Pro Lys Lys Thr Ile Tyr Phe Gly Ala Gly Trp Arg Thr Asp Arg
1               5                   10                  15

Gln Asn Lys Ala Tyr Lys Glu Ala Met Glu Ala Leu Lys Glu Asn Pro
                20                  25                  30

Thr Ile Asp Leu Glu Asn Ser Tyr Val Pro Leu Asp Asn Gln Tyr Lys
            35                  40                  45

Gly Ile Arg Val Asp Glu His Pro Glu Tyr Leu His Asp Lys Val Trp
        50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Gln Gly Gly Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
            115                 120                 125

Val Ser Asp Asn Val Ile Lys Met Ser Gln Leu Lys Asp Phe Asn Phe
        130                 135                 140

Asn Lys Pro Arg Phe Asp Phe Tyr Glu Gly Ala Val Arg
145                 150                 155

<210> SEQ ID NO 43
<211> LENGTH: 157
<212> TYPE: PRT
<213> ORGANISM: artificial
<220> FEATURE:
<223> OTHER INFORMATION: amino acid sequence of PDTT6
      (G92/S123/R13/S93/R157/Q91)

<400> SEQUENCE: 43

Met Pro Lys Lys Thr Ile Tyr Phe Gly Ala Gly Trp Arg Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Asp Lys Val Trp
    50                  55                  60

Ala Thr Ala Thr Tyr Asn Asn Asp Leu Asn Gly Ile Lys Thr Asn Asp
65                  70                  75                  80

Ile Met Leu Gly Val Tyr Ile Pro Asp Glu Gln Gly Ser Gly Leu Gly
                85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Ser Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Arg
145                 150                 155

<210> SEQ ID NO 44
<211> LENGTH: 471
<212> TYPE: DNA
<213> ORGANISM: artificial
<220> FEATURE:
<223> OTHER INFORMATION: nucleotide sequence encoding PDTT3 (SEQ ID
      NO:38)

<400> SEQUENCE: 44
atgccaaaaa agacgatcta cttcggtgcc ggctggcgca ctgaccgcca aaacaaagcc      60
tacaaggaag ccatggaagc cctcaaggaa aacccaacga ttgacctgga aaacagctac     120
gttcccctgg acaaccagta caagggtatc cgggttgatg aacacccgga atacctgcat     180
gacaaggttt gggctacggc cacctacaac aacgacttga acgggatcaa gaccaacgac     240
atcatgctgg gtgtctacat ccctgacgaa cagggccccg gcctgggcat ggaactgggt     300
tacgccttga gccaaggcaa gtacgtcctt ttggtcatcc cggacgaaga ctacggcaag     360
ccgatcagcc tcatgagctg gggcgtcagc gacaacgtga tcaagatgag ccagctgaag     420
gacttcaact tcaacaagcc gcgcttcgac ttctacgaag gtgccgtaaa g              471

```
<210> SEQ ID NO 45
<211> LENGTH: 471
<212> TYPE: DNA
<213> ORGANISM: artificial
<220> FEATURE:
<223> OTHER INFORMATION: nucleotide sequence encoding PDTT3b (SEQ ID
      NO:39)

<400> SEQUENCE: 45
atgccaaaaa agacgatcta cttcggtgcc ggctggcgca ctgaccgcca aaacaaagcc      60
tacaaggaag ccatggaagc cctcaaggaa aacccaacga ttgacctgga aaacagctac     120
gttcccctgg acaaccagta caagggtatc cgggttgatg aacacccgga atacctgcat     180
gacaaggttt gggctacggc cacctacaac aacgacttga acgggatcaa gaccaacgac     240
atcatgctgg gtgtctacat ccctgacgaa cagggcagcg gcctgggcat ggaactgggt     300
tacgccttga gccaaggcaa gtacgtcctt ttggtcatcc cggacgaaga ctacggcaag     360
ccgatcagcc tcatgagctg gggcgtcagc gacaacgtga tcaagatgag ccagctgaag     420
gacttcaact tcaacaagcc gcgcttcgac ttctacgaag gtgccgtaaa g              471

<210> SEQ ID NO 46
<211> LENGTH: 471
<212> TYPE: DNA
<213> ORGANISM: artificial
<220> FEATURE:
<223> OTHER INFORMATION: nucleotide sequence encoding PDTT4 (SEQ ID
      NO:40)

<400> SEQUENCE: 46
atgccaaaaa agacgatcta cttcggtgcc ggctggcgca ctgaccgcca aaacaaagcc      60
tacaaggaag ccatggaagc cctcaaggaa aacccaacga ttgacctgga aaacagctac     120
gttcccctgg acaaccagta caagggtatc cgggttgatg aacacccgga atacctgcat     180
gacaaggttt gggctacggc cacctacaac aacgacttga acgggatcaa gaccaacgac     240
atcatgctgg gtgtctacat ccctgacgaa cagggcggcg gcctgggcat ggaactgggt     300
tacgccttga gccaaggcaa gtacgtcctt ttggtcatcc cggacgaaga ctacggcaag     360
ccgatcagcc tcatgagctg gggcgtcagc gacaacgtga tcaagatgag ccagctgaag     420
gacttcaact tcaacaagcc gcgcttcgac ttctacgaag gtgccgtaaa g              471

<210> SEQ ID NO 47
<211> LENGTH: 471
<212> TYPE: DNA
<213> ORGANISM: artificial
<220> FEATURE:
<223> OTHER INFORMATION: nucleotide sequence encoding PDTT5 (SEQ ID
      NO:41)

<400> SEQUENCE: 47
atgccaaaaa agacgatcta cttcggtgcc ggctggcgca ctgaccgcca aaacaaagcc      60
tacaaggaag ccatggaagc cctcaaggaa aacccaacga ttgacctgga aaacagctac     120
gttcccctgg acaaccagta caagggtatc cgggttgatg aacacccgga atacctgcat     180
gacaaggttt gggctacggc cacctacaac aacgacttga acgggatcaa gaccaacgac     240
atcatgctgg gtgtctacat ccctgacgaa cagggccccg gcctgggcat ggaactgggt     300
tacgccttga gccaaggcaa gtacgtcctt ttggtcatcc cggacgaaga ctacggcaag     360
ccgatcagcc tcatgagctg gggcgtcagc gacaacgtga tcaagatgag ccagctgaag     420
gacttcaact tcaacaagcc gcgcttcgac ttctacgaag gtgccgtaag g              471
```

<210> SEQ ID NO 48
<211> LENGTH: 471
<212> TYPE: DNA
<213> ORGANISM: artificial
<220> FEATURE:
<223> OTHER INFORMATION: nucleotide sequence encoding PDTT7 (SEQ ID
      NO:42)

<400> SEQUENCE: 48

```
atgccaaaaa agacgatcta cttcggtgcc ggctggcgca ctgaccgcca aaacaaagcc       60
tacaaggaag ccatggaagc cctcaaggaa aacccaacga ttgacctgga aaacagctac      120
gttcccctgg acaaccagta caagggtatc cgggttgatg aacacccgga atacctgcat     180
gacaaggttt gggctacggc cacctacaac aacgacttga acgggatcaa gaccaacgac     240
atcatgctgg gtgtctacat ccctgacgaa cagggcggcg gcctgggcat ggaactgggt     300
tacgccttga gccaaggcaa gtacgtcctt ttggtcatcc cggacgaaga ctacggcaag     360
ccgatcagcc tcatgagctg gggcgtcagc gacaacgtga tcaagatgag ccagctgaag     420
gacttcaact tcaacaagcc gcgcttcgac ttctacgaag gtgccgtaag g              471
```

<210> SEQ ID NO 49
<211> LENGTH: 471
<212> TYPE: DNA
<213> ORGANISM: artificial
<220> FEATURE:
<223> OTHER INFORMATION: nucleotide sequence encoding PDTT6 (SEQ ID
      NO:43)

<400> SEQUENCE: 49

```
atgccaaaaa agacgatcta cttcggtgcc ggctggcgca ctgaccgcca aaacaaagcc       60
tacaaggaag ccatggaagc cctcaaggaa aacccaacga ttgacctgga aaacagctac      120
gttcccctgg acaaccagta caagggtatc cgggttgatg aacacccgga atacctgcat     180
gacaaggttt gggctacggc cacctacaac aacgacttga acgggatcaa gaccaacgac     240
atcatgctgg gtgtctacat ccctgacgaa cagggcagcg gcctgggcat ggaactgggt     300
tacgccttga gccaaggcaa gtacgtcctt ttggtcatcc cggacgaaga ctacggcaag     360
ccgatcagcc tcatgagctg gggcgtcagc gacaacgtga tcaagatgag ccagctgaag     420
gacttcaact tcaacaagcc gcgcttcgac ttctacgaag gtgccgtaag g              471
```

PHOSPHODEOXYRIBOSYL TRANSFERASE MUTANT ENZYMES AND USES THEREOF

BACKGROUND OF THE INVENTION

DNA in all known cells and viruses is synthesized from deoxynucleoside triphosphates (dNTPs), the precursor substrates that are condensed by DNA polymerase enzymes, releasing pyrophosphate as co-product. No exception to this biosynthetic scheme was ever encountered in nature, whether nucleoside triphosphates are condensed in response to a DNA template acting as co-catalyst, an RNA template or no template at all. The pyrimidine and purine base moieties attached to the common triphosphodeoxyribosyl moiety of dNTPs are not universally conserved in nature. In addition to the four canonical dNTPs, four noncanonical dNTPs (also called "analogs") bearing an exotic pyrimidine and one bearing an exotic purine were found to be condensed by bacterial viruses (Warren R. A., *Annu. Rev. Microbiol.* 1980).

The demand for purified deoxyribonucleotides is high for example for DNA synthesis (PCR, DNA chip, etc.) and for reverse transcription in vitro in academic research and medical diagnosis. It extends to numerous nucleoside/nucleotide analogues that are used for in vitro DNA mutagenesis, for DNA labeling, or studying nucleotide metabolic enzymes. In parallel, these modified precursors are also used as antibiotics, antiviral and anticancer agents. The diversification of the "bio-compatible nucleotides" is also a field in expansion with the development of synthetic biology as illustrated by the development of new functional base pairs (Khakshoor O. and Kool E. T., *Chem. Commun.* 2011) or the chemical synthesis and assembly of genomes (Gibson et al., *Science* 2010; Gibson et al, *Nat. Methods*, 2010).

Methods for chemical synthesis of nucleotides are evolving but nucleotides are still difficult to make, isolate and characterize (Burgess. K. and Cook D. *Chem. Rev.* 2000). Enzyme-mediated syntheses of natural nucleosides and of some analogs (Burgess. K. and Cook D. *Chem. Rev.* 2000; Mikhailopulo I. A. and Miroshnikov A. I., *Mendeleev Commun* 2011) have been developed using whole cells or coupled enzymes but the available repertoire of enzymes is still limited.

In fact, the enzymatic synthesis of pure 2'-deoxyribonucleotides and the metabolic engineering for producing such compounds is hindered by the intricacy of biosynthesis and salvage pathways, upstream and downstream of the DNA polymerization step. Each nucleobase (A, C, G, T) is naturally processed separately by highly discriminating enzymes that phosphorylate nucleoside monophosphates into diphosphates. This first step of deoxyribonucleoside phosphorylation is highly specific and, in human, four kinases are required: TK1, TK2, dGK and dCK (Eriksson S. et al, *Cell Mol Life Sci* 2002). Furthermore, an enzyme, the nucleotide reductase, connects RNA to DNA precursor biosynthesis by converting the ribose into the deoxyribose moiety (rNDP into dNDP or rNTP into dNTP, depending on nucleotide reductase family) through a cumbersome and fragile free-radical mechanism (Nordlund P. and Reichard P., *Annu. Rev. Biochem.* 2006).

Moreover, chemical phosphorylation requires several steps of protection, deprotection and purification (Johnson D. C., et al, *Curr. Protoc. Nucleic Acid Chem,* 2004). It is only recently that a one-pot synthesis of deoxyribonucleoside 5'-triphosphates without any protection on the nucleosides was reported (Caton-Williams J. et al, *Org. lett.* 2011). Enzymatic methods using deoxyribonucleosides 5'-monophosphate (dNMP) have been attempted but they require dNMP kinases and pyruvate kinases (Bao J. et al, *Biotechnol.* 2007; Ladner W. E. et al, *J. Org. Chem.* 1985).

This complex mechanism renders in vitro dNTPs synthesis very difficult, as it necessitates the use of several enzymes, each of them having only specific substrates and conducting tightly controlled reactions.

There is therefore an urgent need to identify new mechanisms of nucleoside synthesis, e.g., new enzymes that can be more easily reduced to practice, so as to generate new (or common) nucleosides of interest and thereby expand in vitro synthetic DNA chemistry. In particular, as the first limiting step of generating dNTPs or analogs thereof is deoxynucleoside phosphorylation, there is an urgent need to identify enzymes that are able to efficiently exchange deoxyribose mono-, di-, or tri-phosphate between any kind of nucleobases.

In this context, the present inventors identified new enzymes that are able to transfer 5'-phosphorylated deoxyribose between two nucleobases (N, N'), according to the following formula I:

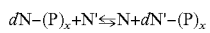

where 'x' stands for 0, 1, 2 or 3. These enzymes are not substrate-specific as they are able to transfer said deoxyribose moiety between any nucleobase (A, T, G, or C), would it be canonical or not (analogs). Moreover, these enzymes have advantageous mono-, di-, and triphosphodeoxyribosyl-transferase activities. They are therefore very promising tools for synthesizing various dNTPs or analogs thereof. The use of these enzymes therefore opens the road to new synthetic pathways of deoxyribonucleotides.

FIGURE LEGENDS

FIG. 1 discloses the reaction which is catalysed by the NDT enzyme (up) and the Rcl enzyme (down).

Figure 2:
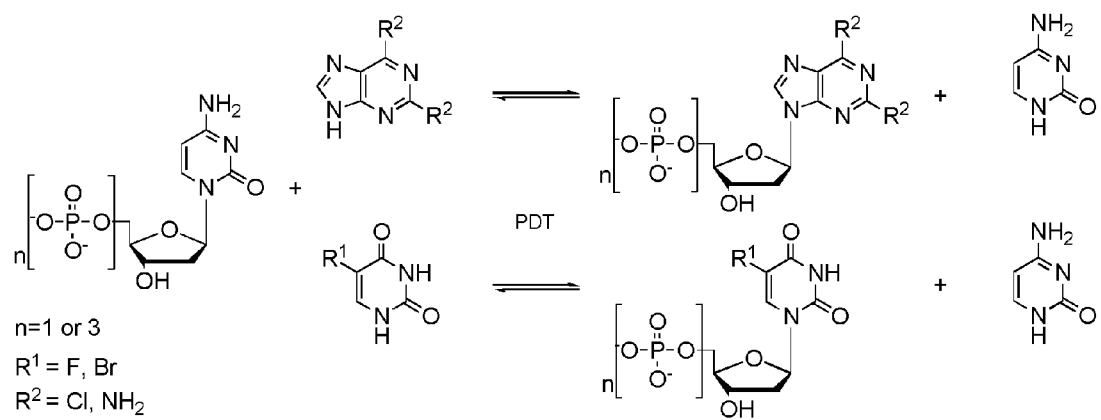

FIG. 2 discloses examples of reactions catalyzed by the mutant enzymes of the invention, the so-called PDTM4, PDTM5 and/or PDTT2 mutants.

DETAILED DESCRIPTION OF THE INVENTION

The new enzymes of the invention were built using a structure-based and stepwise approach based on the analysis of two distantly related enzymes: a nucleoside deoxyribosyltransferase (EC 2.4.2.6) (hereafter called "NDT") from a *Lactobacilli* species and a 5'-monophosphate-2'-deoxyribonucleoside hydrolase (EC 3.2.2.-) from rat (hereafter called "Rcl") (see FIG. 1). The sequence of this NDT enzyme is disclosed in the enclosed listing under the reference SEQ ID NO:1. The sequence of this Rcl enzyme is disclosed in the enclosed listing under the reference SEQ ID NO:2. Although, their sequences are globally dissimilar (~18% of sequence identity), these two proteins differ in their oligomerization state (NDT is an hexamer, whereas Rcl is a dimer), adopt the same Rossmann fold, and share a common catalytic triad. Both enzymes hydrolyze their substrates via the formation of a deoxyribose(5-phosphate)-enzyme covalent intermediate (Doddapaneni K. et al, *Biochemistry* 2011; Porter D. J., et al, *J. Biol. Chem.* 1995) using a conserved glutamate residue (Porter D. J., et al, *J. Biol. Chem.* 1995). However, these enzymes differ functionally: NDT can act as a transferase on nucleoside (x=0 in the formula I above) while Rcl hydrolyse monophosphate deoxynucleoside (x=1 in the formula I above) (Ghiorghi Y. K. et al, *J. Biol. Chem.*

2007) (see also FIG. 1). These structural and functional features are in agreement with Rcl and NDT diverging from a common enzyme ancestor with a broader substrate specificity.

The nucleoside deoxyribosyltransferase enzyme family contains hydrolases and transferases with different substrate specificities. In particular, previous studies on N-deoxyribosyltransferases revealed that these enzymes have a broad tolerance toward modifications of the purine or pyrimidine. In contrast, they have a strict specificity for 2-deoxyribose as a carbohydrate moiety even if purine 4'-thionucleosides have been synthesized using *L. leichmannii* NDT (Freeman G. A. et al, *Bioorg. Med. Chem* 1995). It was also known that a single mutation was sufficient to enlarge the specificity of NDT to 2,3-dideoxyribose and to 2,3-didehydro-2-, 3-dideoxyribose (Kaminski P. A. et al, *J. Biol. Chem.* 2008), suggesting that the plasticity of NDT was even more important than initially thought.

The results of the present inventors herein show that the conservation of overall topology and of the catalytic mechanism of the members of the N-deoxyribosyltransferase enzyme family is essential information to guide the design of phopsphodeoxyribosyltransferase enzymes of interest. As reported by Gerlt and Babbitt (*Curr. Opinion Chem. Biol.* 2009), "few successes in enzyme (re)design were reported although many have been attempted". The present work exemplifies how natural evolution can be rewired to design novel biocatalysts.

Description of the Mutants of the Invention

The NDT enzyme of the *Lactobacillus leichmannii* bacterial species SEQ ID NO:1 was chosen as a starting template.

The inventors discovered that two amino acids, D92 and N123 of NDT, can be advantageously substituted into small serines, leading to the generation of the two following mutants:

The so-called "PDTM1" mutant (for "phosphodeoxyribosyltransferase monophosphate 1") corresponding to the NDT single mutant D92S (the Aspartic acid in position 92 being replaced by a Serine amino acid), said mutant having the SEQ ID NO:3, and The so-called "PDTM2" mutant (for "phosphodeoxyribosyltransferase monophosphate 2") corresponding to the NDT double mutant D92S, N123S (the Asparagine amino acid in position 123 being replaced by a Serine amino acid), said mutant having the sequence SEQ ID NO:4.

These two mutants are able to transfer deoxyribose 5-phosphate between cytosine and adenine, although with a low efficiency (see examples below).

The inventors moreover found that it was advantageous to replace D92 by a Glycine (G), and the Valine amino acid at position 93 by a Threonine (T), in order to remove a negatively charged residue and simultaneously make the backbone amide groups more accessible to better accommodate a phosphate group. Interestingly, they further showed that it is also possible to obtain a similar result by replacing both D92 by a Glycine (G), and the Valine amino acid at position 93 by a Proline (P), or by replacing both D92 by a Glycine (G), and the Valine amino acid at position 93 by a Glutamine (G), or by replacing both D92 by a Glycine (G), and the Valine amino acid at position 93 by a Serine (S). Mutant enzymes harboring these combinations of mutations are all able to transfer deoxyribose 5-phosphate between cytosine and adenine with a high efficiency (see examples below).

These substitutions lead to the generation of the two following mutants:

A mutant enzyme whose amino acid sequence is SEQ ID NO:1, in which the amino acid at position 92 is replaced by a Glycine (G) and the amino acid at position 93 is replaced by a Threonine (T), A mutant enzyme, whose amino acid sequence is SEQ ID NO:1, in which the amino acid at position 92 is replaced by a Glycine (G), the amino acid at position 93 is replaced by a Threonine (T) and the amino acid at position 123 is replaced by a Serine (S).

The inventors further highlighted that it was advantageous to substitute amino acid F13 into the positively charged arginine amino acid (R) or into the polar but neutral glutamine amino acid (Q).

This substitution led to the generation of the three following mutants:

The so-called "PDTM3" mutant (for "phosphodeoxyribosyltransferase monophosphate 3") corresponding to the PDTM1 mutant SEQ ID NO:3 in which the Phenylalanine in position 13 is replaced by an Arginine (R), said PDTM3 mutant having the sequence SEQ ID NO:5, The so-called "PDTM4" mutant (for "phosphodeoxyribosyltransferase monophosphate 4"), corresponding to the PDTM2 mutant SEQ ID NO:4 in which the Phenylalanine in position 13 has been replaced by an Arginine (R), said PDTM4 mutant having the sequence SEQ ID NO:6, and The so-called "PDTM5" mutant (for "phosphodeoxyribosyltransferase monophosphate 5"), corresponding to the PDTM2 mutant SEQ ID NO:4 in which the Phenylalanine in position 13 has been replaced by a Glutamine (Q), said PDTM5 mutant having the sequence SEQ ID NO:7.

As shown in the experimental part below, the PDTM 3, 4 and 5 mutants show an enhanced deoxyribose 5-phosphate transferase activity between the nucleobases C and A. This improvement is mainly due to a better affinity for dCMP, the $K_m$ for dCMP varying from 22 mM (PDTM3) to 11 or 12 mM (PDTM4 and PDTM5 respectively).

Also, it has been observed that the phosphodeoxyribosyltransferase activity of these mutants is not restricted to cytosine as donor and to adenine as acceptor. The PDTM3 mutant is indeed able to transfer deoxyribose 5-phosphate between the nucleobases A and C, and C and T, and the PDTM4 mutant is two times more active than PDTM3 (whatever the couple of bases tested). And the PDTM5 mutant transfers deoxyribose 5-phosphate efficiently between the nucleobases C and A, and A and C.

In a particular embodiment, a mutant enzyme, whose amino acid sequence is SEQ ID NO:1 in which the amino acid at position 92 is replaced by a Serine (S) and the amino acid at position 13 is replaced by a Glutamine (Q), is encompassed in the present invention (PDTM3bis).

Moreover, replacing the two amino acids DV by GT at positions 92 to 93 in PDTM3 and PDTM3bis leads to the generation of the following mutants:

A mutant enzyme whose amino acid sequence is SEQ ID NO:1 in which the amino acid at position 92 is replaced by a Glycine (G), the amino acid at position 93 is replaced by a Threonine (T) and the amino acid at position 13 is replaced by an Arginine (R).

A mutant enzyme whose amino acid sequence is SEQ ID NO:1 in which the amino acid at position 92 is replaced by a Glycine (G), the amino acid at position 93 is replaced by a Threonine (T) and the amino acid at position 13 is replaced by a Glutamine (Q).

Moreover, the double substitution DV to GT in PDTM4 led to the generation of the enzyme mutant called "PDTT0" (for "phosphodeoxyribosyltransferase triphosphate 0") having the sequence SEQ ID NO:8, and corresponding to SEQ ID NO:1 in which i) the Aspartic acid at position 92 has been replaced by a Glycine (G), ii) the Phenylalanine amino acid at position 13 has been replaced by an Arginine (R), iii) the Asparagine amino acid at position 123 has been replaced by a Serine (S), and iv) the Valine amino acid at position 93 has been replaced by a Threonine (T).

Substitution of the amino acid at position 13 by a Glutamine (Q) in PDTT0 leads to the generation of another mutant enzyme which is encompassed in the present invention (PDTT0bis). This mutant enzyme has the amino acid sequence SEQ ID NO:1, in which the amino acid at position 92 is replaced by a Glycine (G), the amino acid at position 93 is replaced by a Threonine (T), the amino acid at position 13 is replaced by a Glutamine (Q), and the amino acid at position 123 is replaced by a Serine (S).

The inventors then identified that it was possible to favor further the entrance of nucleotides by adding a positively charged residue or by removing a negative one, for example by (i) replacing the Glutamic acid at position 91 by a Glutamine (Q); and/or (ii) by replacing the Tyrosine amino acid at position 157 by a Lysine (K).

This led respectively to the generation of the two following enzyme mutants:
The so-called "PDTT1" mutant (for "phosphodeoxyribosyltransferase triphosphate 1"), corresponding to the PDTT0 mutant SEQ ID NO:8, in which the Tyrosine amino acid at position 157 has been replaced by a Lysine (K), said PDTT1 mutant having the sequence SEQ ID NO:9, and
The so-called "PDTT2" mutant (for "phosphodeoxyribosyltransferase triphosphate 2"), corresponding to the PDTT0 mutant SEQ ID NO:8, in which the Glutamic Acid at position 91 has been replaced by a Glutamine (Q), said PDTT2 mutant having the sequence SEQ ID NO:10.

Importantly, the enzyme mutants PDTT1 and PDTT2 have the unique property of transferring deoxyribose 5-mono, -di, -triphosphate and 1-thiotriphosphate moieties between various nucleobases, including non-natural nucleobases (see the experimental results below). This property is unlikely to exist in nature since nucleotide metabolic enzymes are highly specialized and recognize usually one particular substrate.

Further mutations in the so-called "PDTT1" mutant lead to several enzymes of interest, in particular:
The so-called "PDTT1ter" mutant, corresponding to the PDTT1 mutant SEQ ID NO:9, in which the Arginine amino acid at position 13 has been replaced by a Glutamine (Q), said PDTT1ter mutant having the sequence SEQ ID NO:35, and
The so-called "PDTT1quinquies" mutant, corresponding to the PDTT1 mutant SEQ ID NO:9, in which the Glutamine amino acid at position 92 has been replaced by a Serine (S), the Arginine amino acid at position 13 has been replaced by a Glutamine (Q), the Threonine amino acid at position 93 has been replaced by a Valine (V), and the Glutamic acid at position 91 has been replaced by a Glutamine (Q), said PDTT1quinquies mutant having the sequence SEQ ID NO:36, and
The so-called "PDTT1sexies" mutant, corresponding to the PDTT1 mutant SEQ ID NO:9, in which the Arginine amino acid at position 13 has been replaced by a Glutamine (Q) and the Glutamic acid at position 91 has been replaced by a Glutamine (Q), said PDTT1sexies mutant having the sequence SEQ ID NO:37.

Further, the inventors have discovered that the ability to transfer triphosphate moieties between various nucleobases could also be obtained with alternatives mutations in the so-called "PDTT2" mutant. In particular, the G92/T93 mutations could advantageously be replaced by G92/P93, or G92/G93 or G92/S93 mutation without a loss of function. Moreover, the inventors found that when the Tyrosine amino acid at position 157 was replaced by a Lysine (K), in addition with the above-mentioned mutations G92/P93, or G92/G93 or G92/S93, the catalytic activity of the enzyme mutants was increased, as shown in the experimental part hereafter (tables 4 and 5 in particular).

This led in particular to the generation of the following enzyme mutants:
The so-called "PDTT3" mutant (for "phosphodeoxyribosyltransferase triphosphate 3"), corresponding to the PDTT2 mutant SEQ ID NO:10, in which the Threonine at position 93 has been replaced by a Proline (P), and the Tyrosine amino acid at position 157 has been replaced by a Lysine (K), said PDTT3 mutant having the sequence SEQ ID NO:38,
The so-called "PDTT3b" mutant (for "phosphodeoxyribosyltransferase triphosphate 3b"), corresponding to the PDTT2 mutant SEQ ID NO:10, in which the Threonine at position 93 has been replaced by a Glutamine (G), and the Tyrosine amino acid at position 157 has been replaced by a Lysine (K), said PDTT3b mutant having the sequence SEQ ID NO:39, and
The so-called "PDTT4" mutant (for "phosphodeoxyribosyltransferase triphosphate 4"), corresponding to the PDTT2 mutant SEQ ID NO:10, in which the Threonine at position 93 has been replaced by a Serine (S), and the Tyrosine amino acid at position 157 has been replaced by a Lysine (K), said PDTT4 mutant having the sequence SEQ ID NO:40.

Finally, the inventors have discovered that mutations of the Lysine amino acid at position 157 by an Arginine (R) in the so-called "PDTT3", "PDTT3b", and "PDTT4" mutants could significantly increase the catalytic activity of the mutant enzymes of the invention. This led respectively to the generation of the following enzyme mutants:
The so-called "PDTT5" mutant (for "phosphodeoxyribosyltransferase triphosphate 5"), corresponding to the PDTT3 mutant SEQ ID NO: 38, in which the Lysine amino acid at position 157 has been replaced by an Arginine (R), said PDTT5 mutant having the sequence SEQ ID NO:41,
The so-called "PDTT7" mutant (for "phosphodeoxyribosyltransferase triphosphate 7"), corresponding to the PDTT3b mutant SEQ ID NO:39, in which the Lysine amino acid at position 157 has been replaced by an Arginine (R), said PDTT7 mutant having the sequence SEQ ID NO:42, and
The so-called "PDTT6" mutant (for "phosphodeoxyribosyltransferase triphosphate 6"), corresponding to the PDTT4 mutant SEQ ID NO:40, in which the Lysine amino acid at position 157 has been replaced by an Arginine (R), said PDTT6 mutant having the sequence SEQ ID NO:43.

To conclude, the present inventors discovered for the first time enzyme mutants that do not exist naturally and have never been disclosed so far. These new enzymes are useful for synthetizing various nucleosides or analogs thereof in vitro or in vivo. They thus appear to be of great interest.

In a first aspect, the present invention therefore targets a mutant phosphodeoxyribosyltransferase enzyme, whose amino acid sequence is SEQ ID NO:1, in which the Aspartic acid at position 92 is replaced by a Serine (S) or a Glycine (G), provided that, when the Aspartic acid at position 92 is replaced by a Glycine (G), the Valine amino acid at position 93 is replaced by a Threonine (T).

Moreover, when the Aspartic acid at position 92 is replaced by a Glycine (G), the Valine amino acid at position 93 can also advantageously be replaced by a Proline (P), or a Serine (S) or a Glycine (G).

Thus, another aspect of the invention is a mutant phosphodeoxyribosyltransferase enzyme, whose amino acid sequence is SEQ ID NO:1, in which the Aspartic acid at position 92 is replaced by a Serine (S) or a Glycine (G), provided that, when the Aspartic acid at position 92 is replaced by a Glycine (G), the Valine amino acid at position 93 is replaced by a Threonine (T), or a Proline (P), or a Serine (S) or a Glycine (G).

The said mutant enzyme has for example the amino acid sequence SEQ ID NO:3, corresponding to SEQ ID NO:1 in which the amino acid at position 92 is replaced by a Serine (S).

The mutant enzyme of the invention can also have the amino acid sequence SEQ ID NO:1, in which the amino acid at position 92 is replaced by a Glycine (G) and the amino acid at position 93 is replaced by a Threonine (T).

Alternatively, the mutant enzyme of the invention can have the amino acid sequence SEQ ID NO:1, in which the amino acid at position 92 is replaced by a Glycine (G) and the amino acid at position 93 is replaced by a Proline (P).

In another embodiment of the invention, the mutant enzyme of the invention can have the amino acid sequence SEQ ID NO:1, in which the amino acid at position 92 is replaced by a Glycine (G) and the amino acid at position 93 is replaced by a Serine (S).

In yet another embodiment of the invention, the mutant enzyme of the invention can have the amino acid sequence SEQ ID NO:1, in which the amino acid at position 92 is replaced by a Glycine (G) and the amino acid at position 93 is replaced by a Glycine (G).

In a preferred embodiment, the mutant enzyme of the invention further comprises at least one, preferably at least two, more preferably at least three, and even more preferably at least four mutation(s) selected in the group consisting of:
(1) the Asparagine amino acid at position 123 is replaced by Serine (S);
(2) the Phenylalanine amino acid at position 13 is replaced by an Arginine (R) or a Glutamine (Q);
(3) the Glutamic acid at position 91 is replaced by a Glutamine (Q); and
(4) the Tyrosine amino acid at position 157 is replaced by a Lysine (K).

In addition, the inventors have demonstrated that the Tyrosine amino acid at position 157 can advantageously be replaced by an Arginine (R). Enzymes which harbor this mutation have an increased catalytic activity compared to both the wild type NDT enzyme, and corresponding mutant enzymes of the invention in which the Tyrosine amino acid at position 157 is replaced by a Lysine (K).

Hence, in another preferred embodiment, the mutant enzyme of the invention further comprises at least one, preferably at least two, more preferably at least three, and even more preferably at least four mutation(s) selected in the group consisting of:
(1) the Asparagine amino acid at position 123 is replaced by Serine (S);
(2) the Phenylalanine amino acid at position 13 is replaced by an Arginine (R) or a Glutamine (Q);
(3) the Glutamic acid at position 91 is replaced by a Glutamine (Q); and
(4) the Tyrosine amino acid at position 157 is replaced by a Lysine (K) or an Arginine (R).

In particular, the mutant enzyme of the invention may comprise one of the above-mentioned mutations (1) to (4), in addition to 92S or 92G/93T.

In this case, the mutant enzyme of the invention has for example the amino acid sequence SEQ ID NO:4, corresponding to SEQ ID NO:1 in which the amino acid at position 92 is replaced by a Serine (S) and the amino acid at position 123 is replaced by a Serine (S).

The mutant enzyme of the invention may also have the amino acid sequence SEQ ID NO:5, corresponding to SEQ ID NO:1 in which the amino acid at position 92 is replaced by a Serine (S) and the amino acid at position 13 is replaced by an Arginine (R).

The present invention also targets:
A mutant enzyme whose amino acid sequence is SEQ ID NO:1 in which the amino acid at position 92 is replaced by a Serine (S) and the amino acid at position 157 is replaced by a Lysine (K),
A mutant enzyme whose amino acid sequence is SEQ ID NO:1 in which the amino acid at position 92 is replaced by a Serine (S) and the amino acid at position 91 is replaced by a Glutamine (Q),
A mutant enzyme whose amino acid sequence is SEQ ID NO:1 in which the amino acid at position 92 is replaced by a Serine (S) and the amino acid at position 157 is replaced by an Arginine (R),
A mutant enzyme whose amino acid sequence is SEQ ID NO:1, in which the amino acid at position 92 is replaced by a Glycine (G), the amino acid at position 93 is replaced by a Threonine (T), and the amino acid at position 157 is replaced by a Lysine (K),
A mutant enzyme whose amino acid sequence is SEQ ID NO:1, in which the amino acid at position 92 is replaced by a Glycine (G), the amino acid at position 93 is replaced by a Threonine (T), and the amino acid at position 91 is replaced by a Glutamine (Q), and
A mutant enzyme whose amino acid sequence is SEQ ID NO:1, in which the amino acid at position 92 is replaced by a Glycine (G), the amino acid at position 93 is replaced by a Threonine (T), and the amino acid at position 157 is replaced by an Arginine (R).

In another embodiment, the mutant enzyme of the invention may comprise one of the above-mentioned mutations (1) to (4), in addition to 92G/93P, 92G/93S, or 92G/93G.

The present invention thus also targets:
A mutant enzyme whose amino acid sequence is SEQ ID NO:1, in which the amino acid at position 92 is replaced by a Glycine (G), the amino acid at position 93 is replaced by a Proline (P) and the amino acid at position 123 is replaced by Serine (S),
A mutant enzyme whose amino acid sequence is SEQ ID NO:1, in which the amino acid at position 92 is replaced by a Glycine (G), the amino acid at position 93 is replaced by a Serine (S) and the amino acid at position 123 is replaced by Serine (S), A mutant enzyme whose amino acid sequence is SEQ ID NO:1, in which the amino acid at position 92 is replaced by a Glycine (G), the amino acid at position 93 is replaced by a Glycine (G) and the amino acid at position 123 is replaced by Serine (S), A mutant enzyme whose amino acid sequence is SEQ ID NO:1, in which the amino acid at position 92 is replaced by a Glycine (G), the amino acid at position 93 is replaced by a Proline (P) and the amino acid at position 13 is replaced by an Arginine (R), A mutant enzyme whose amino acid sequence is SEQ ID NO:1, in which the amino acid at position 92 is replaced by a Glycine (G), the amino acid at position 93 is replaced by a Serine (S) and the amino acid at position 13 is replaced by an Arginine (R), A mutant enzyme whose amino acid sequence is SEQ ID NO:1, in which the amino acid at position 92 is replaced by a Glycine (G), the amino acid at position 93 is replaced by a Glycine (G) and the amino acid at position 13 is replaced by an Arginine (R), A mutant enzyme whose amino acid sequence is SEQ ID NO:1, in which the amino acid at position 92 is replaced by a Glycine (G), the amino acid at position 93 is replaced by a Proline (P) and the amino acid at position 13 is replaced by a Glutamine (Q), A mutant enzyme whose amino acid sequence is SEQ ID NO:1, in which the amino acid at position 92 is replaced by a Glycine (G), the amino acid at position 93 is replaced by a Serine (S) and the amino acid at position 13 is replaced by a Glutamine (Q), A mutant enzyme whose amino acid sequence is SEQ ID NO:1, in which the amino acid at position 92 is replaced by a Glycine (G), the amino acid at position 93 is replaced by a Glycine (G) and the amino acid at position 13 is replaced by a Glutamine (Q), A mutant enzyme whose amino acid sequence is SEQ ID NO:1, in which the amino acid at position 92 is replaced by a Glycine (G), the amino acid at position 93 is replaced by a Proline (P) and the amino acid at position 91 is replaced by a Glutamine (Q), A mutant enzyme whose amino acid sequence is SEQ ID NO:1, in which the amino acid at position 92 is replaced by a Glycine (G), the amino acid at position 93 is replaced by a Serine (S) and the amino acid at position 91 is replaced by a Glutamine (Q), A mutant enzyme whose amino acid sequence is SEQ ID NO:1, in which the amino acid at position 92 is replaced by a Glycine (G), the amino acid at position 93 is replaced by a Glycine (G) and the amino acid at position 91 is replaced by a Glutamine (Q), A mutant enzyme whose amino acid sequence is SEQ ID NO:1, in which the amino acid at position 92 is replaced by a Glycine (G), the amino acid at position 93 is replaced by a Proline (P) and the amino acid at position 157 is replaced by a Lysine (K), A mutant enzyme whose amino acid sequence is SEQ ID NO:1, in which the amino acid at position 92 is replaced by a Glycine (G), the amino acid at position 93 is replaced by a Serine (S) and the amino acid at position 157 is replaced by a Lysine (K), A mutant enzyme whose amino acid sequence is SEQ ID NO:1, in which the amino acid at position 92 is replaced by a Glycine (G), the amino acid at position 93 is replaced by a Glycine (G) and the amino acid at position 157 is replaced by a Lysine (K), A mutant enzyme whose amino acid sequence is SEQ ID NO:1, in which the amino acid at position 92 is replaced by a Glycine (G), the amino acid at position 93 is replaced by a Proline (P) and the amino acid at position 157 is replaced by an Arginine (R), A mutant enzyme whose amino acid sequence is SEQ ID NO:1, in which the amino acid at position 92 is replaced by a Glycine (G), the amino acid at position 93 is replaced by a Serine (S) and the amino acid at position 157 is replaced by an Arginine (R), and A mutant enzyme whose amino acid sequence is SEQ ID NO:1, in which the amino acid at position 92 is replaced by a Glycine (G), the amino acid at position 93 is replaced by a Glycine (G) and the amino acid at position 157 is replaced by an Arginine (R).

The mutant enzyme of the invention may also comprise two of the above-mentioned mutations (1) to (4), preferably the mutations (1) and (2), in addition to 92S or 92G/93T. In this case, the mutant enzyme of the invention can have for example the amino acid sequence SEQ ID NO:6, or SEQ ID NO:7, corresponding to SEQ ID NO:1 in which the amino acid at position 92 is replaced by a Serine (S), the amino acid at position 123 is replaced by a Serine (S), and the amino acid at position 13 is replaced by an Arginine (R) or a Glutamine (Q), respectively.

It can also have the amino acid sequence SEQ ID NO:8, corresponding to SEQ ID NO:1 in which the amino acid at position 92 is replaced by a Glycine (G), the amino acid at position 13 is replaced by an Arginine (R), the amino acid at position 123 is replaced by a Serine (S), and the amino acid at position 93 is replaced by a Threonine (T).

The present invention also targets:

A mutant enzyme whose amino acid sequence is SEQ ID NO:1 in which the amino acid at position 92 is replaced by a Serine (S), the amino acid at position 91 is replaced by a Glutamine (Q) and the amino acid at position 157 is replaced by a Lysine (K), A mutant enzyme whose amino acid sequence is SEQ ID NO:1 in which the amino acid at position 92 is replaced by a Serine (S), the amino acid at position 123 is replaced by a Serine (S), and the amino acid at position 157 is replaced by a Lysine (K), A mutant enzyme whose amino acid sequence is SEQ ID NO:1 in which the amino acid at position 92 is replaced by a Serine (S), the amino acid at position 123 is replaced by a Serine (S), and the amino acid at position 91 is replaced by a Glutamine (Q), A mutant enzyme whose amino acid sequence is SEQ ID NO:1 in which the amino acid at position 92 is replaced by a Serine (S), the amino acid at position 13 is replaced by an Arginine (R), and the amino acid at position 157 is replaced by a Lysine (K), A mutant enzyme whose amino acid sequence is SEQ ID NO:1 in which the amino acid at position 92 is replaced by a Serine (S), the amino acid at position 13 is replaced by an Arginine (R), and the amino acid at position 91 is replaced by a Glutamine (Q), A mutant enzyme whose amino acid sequence is SEQ ID NO:1 in which the amino acid at position 92 is replaced by a Serine (S), the amino acid at position 13 is replaced by a Glutamine (Q), and the amino acid at position 91 is replaced by a Glutamine (Q), A mutant enzyme whose amino acid sequence is SEQ ID NO:1 in which the amino acid at position 92 is replaced by a Serine (S), the amino acid at position 13 is replaced by a Glutamine (Q), and the amino acid at position 157 is replaced by a Lysine (K), A mutant enzyme whose amino acid sequence is SEQ ID NO:1, in which the amino acid at position 92 is replaced by a Glycine (G), the amino acid at position 93 is replaced by a Threonine (T), the amino acid at position 91 is replaced by a Glutamine (Q) and the amino acid at position 157 is replaced by a Lysine (K), A mutant enzyme whose amino acid sequence is SEQ ID NO:1, in which the amino acid at position 92 is replaced by a Glycine (G), the amino acid at position 93 is replaced by a Threonine (T), the amino acid at position 123 is replaced by a Serine (S) and the amino acid at position 157 is replaced by a Lysine (K), A mutant enzyme whose amino acid sequence is SEQ ID NO:1, in which the amino acid at position 92 is replaced by a Glycine (G), the amino acid at position 93 is replaced by a Threonine (T), the amino acid at position 123 is replaced by a Serine (S) and the amino acid at position 91 is replaced by a Glutamine (Q), A mutant enzyme whose amino acid sequence is SEQ ID NO:1 in which the amino acid at position 92 is replaced by a Glycine (G), the amino acid at position 93 is replaced by a Threonine (T), the amino acid at position 13 is replaced by an Arginine (R), and the amino acid at position 157 is replaced by a Lysine (K), A mutant enzyme whose amino acid sequence is SEQ ID NO:1 in which the amino acid at position 92 is replaced by a Glycine (G), the amino acid at position 93 is replaced by a Threonine (T), the amino acid at position 13 is replaced by an Arginine (R), and the amino acid at position 91 is replaced by a Glutamine (Q), A mutant enzyme whose amino acid sequence is SEQ ID NO:1 in which the amino acid at position 92 is replaced by a Glycine (G), the amino acid at position 93 is replaced by a Threonine (T), the amino acid at position 13 is replaced by a Glutamine (Q), and the amino acid at position 91 is replaced by a Glutamine (Q), and A mutant enzyme whose amino acid sequence is SEQ ID NO:1 in which the amino acid at position 92 is replaced by a Glycine (G), the amino acid at position 93 is replaced by a Threonine (T), the amino acid at position 13 is replaced by a Glutamine (Q), and the amino acid at position 157 is replaced by a Lysine (K).

The mutant enzyme of the invention may also comprise three of the above-mentioned mutations (1) to (4), preferably at least the mutations (1) and (2), in addition to 92S or 92G/93T.

In this case the mutant enzyme of the invention can have the amino acid sequence SEQ ID NO:9 or SEQ ID NO:10, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Threonine (T), and the amino acid at position 157 is replaced by a Lysine (K) or the amino acid at position 91 is replaced by a Glutamine (Q), respectively.

The present invention also targets:

A mutant enzyme whose amino acid sequence is SEQ ID NO:1 in which the amino acid at position 92 is replaced by a Serine (S), the amino acid at position 123 is replaced by a Serine (S), the amino acid at position 157 is replaced by a Lysine (K) and the amino acid at position 91 is replaced by a Glutamine (Q), A mutant enzyme whose amino acid sequence is SEQ ID NO:1 in which the amino acid at position 92 is replaced by a Serine (S), the amino acid at position 13 is replaced by an Arginine (R), the amino acid at position 157 is replaced by a Lysine (K) and the amino acid at position 91 is replaced by a Glutamine (Q), A mutant enzyme whose amino acid sequence is SEQ ID NO:1 in which the amino acid at position 92 is replaced by a Serine (S), the amino acid at position 13 is replaced by an Glutamine (Q), the amino acid at position 157 is replaced by a Lysine (K) and the amino acid at position 91 is replaced by a Glutamine (Q), A mutant enzyme whose amino acid sequence is SEQ ID NO:1 in which the amino acid at position 92 is replaced by a Serine (S), the amino acid at position 13 is replaced by an Arginine (R), the amino acid at position 123 is replaced by a Serine (S), and the amino acid at position 91 is replaced by a Glutamine (Q), A mutant enzyme whose amino acid sequence is SEQ ID NO:1, in which the amino acid at position 92 is replaced by a Serine (S), the amino acid at position 13 is replaced by a Glutamine (Q), the amino acid at position 123 is replaced by a Serine (S) and the amino acid at position 91 is replaced by a Glutamine (Q), A mutant enzyme whose amino acid sequence is SEQ ID NO:1, in which the amino acid at position 92 is replaced by a Serine (S), the amino acid at position 13 is replaced by a Glutamine (Q), and the amino acid at position 123 is replaced by a Serine (S) and the amino acid at position 157 is replaced by a Lysine (K), A mutant enzyme whose amino acid sequence is SEQ ID NO:1, in which the amino acid at position 92 is replaced by a Glycine (G), the amino acid at position 93 is replaced by a Threonine (T), the amino acid at position 123 is replaced by a Serine (S), the amino acid at position 157 is replaced by a Lysine (K) and the amino acid at position 91 is replaced by a Glutamine (Q), A mutant enzyme whose amino acid sequence is SEQ ID NO:1 in which the amino acid at position 92 is replaced by a Glycine (G), the amino acid at position 93 is replaced by a Threonine (T), the amino acid at position 13 is replaced by an Arginine (R), the amino acid at position 157 is replaced by a Lysine (K) and the amino acid at position 91 is replaced by a Glutamine (Q), A mutant enzyme whose amino acid sequence is SEQ ID NO:1 in which the amino acid at position 92 is replaced by a Glycine (G), the amino acid at position 93 is replaced by a Threonine (T), the amino acid at position 13 is replaced by an Glutamine (Q), the amino acid at position 157 is replaced by a Lysine (K) and the amino acid at position 91 is replaced by a Glutamine (Q), A mutant enzyme whose amino acid sequence is SEQ ID NO:1, in which the amino acid at position 92 is replaced by a Glycine (G), the amino acid at position 93 is replaced by a Threonine (T), the amino acid at position 13 is replaced by a Glutamine (Q), the amino acid at position 123 is replaced by a Serine (S) and the amino acid at position 157 is replaced by a Lysine (K), and A mutant enzyme whose amino acid sequence is SEQ ID NO:1, in which the amino acid at position 92 is replaced by a Glycine (G), the amino acid at position 93 is replaced by a Threonine (T), the amino acid at position 13 is replaced by a Glutamine (Q), the amino acid at position 123 is replaced by a Serine (S) and the amino acid at position 91 is replaced by a Glutamine (Q).

Finally, the mutant enzyme of the invention may also comprise the four above-mentioned mutations (1) to (4), in addition to 92S or 92G/93T.

In this case the mutant enzyme of the invention can have the amino acid sequence SEQ ID NO:35, corresponding to SEQ ID NO:1 in which the amino acid at position 92 is replaced by a Glycine (G), the amino acid at position 13 is replaced by a Glutamine (Q), the amino acid at position 123 is replaced by a Serine (S), the amino acid at position 93 is replaced by a Threonine (T) and the amino acid at position 157 is replaced by a Lysine (K).

The mutant enzyme of the invention can also have the amino acid sequence SEQ ID NO:36, corresponding to SEQ ID NO:1 in which the amino acid at position 92 is replaced by a Serine (S), the amino acid at position 13 is replaced by a Glutamine (Q), the amino acid at position 123 is replaced by a Serine (S), the amino acid at position 91 is replaced by a Glutamine (Q) and the amino acid at position 157 is replaced by a Lysine (K).

Alternatively, the mutant enzyme of the invention can also have the amino acid sequence SEQ ID NO:37, corresponding to SEQ ID NO:1 in which the amino acid at position 92 is replaced by a Glycine (G), the amino acid at position 13 is replaced by a Glutamine (Q), the amino acid at position 123 is replaced by a Serine (S), the amino acid at position 93 is replaced by a Threonine (T), the amino acid at position 91 is replaced by a Glutamine (Q) and the amino acid at position 157 is replaced by a Lysine (K).

The present invention also targets:

A mutant enzyme whose amino acid sequence is SEQ ID NO:1, in which the amino acid at position 92 is replaced by a Serine (S), the amino acid at position 13 is replaced by a Glutamine (Q), the amino acid at position 123 is replaced by a Serine (S), the amino acid at position 91 is replaced by a Glutamine (Q) and the amino acid at position 157 is replaced by a Lysine (K), or A mutant enzyme whose amino acid sequence is SEQ ID NO:1, in which the amino acid at position 92 is replaced by a Serine (S), the amino acid at position 13 is replaced by an Arginine (R), the amino acid at position 123 is replaced by a Serine (S), the amino acid at position 91 is replaced by a Glutamine (Q) and the amino acid at position 157 is replaced by a Lysine (K), or A mutant enzyme whose amino acid sequence is SEQ ID NO:1, in which the amino acid at position 92 is replaced by a Serine (S), the amino acid at position 13 is replaced by a Glutamine (Q), the amino acid at position 123 is replaced by a Serine (S), the amino acid at position 91 is replaced by a Glutamine (Q) and the amino acid at position 157 is replaced by an Arginine (R), or A mutant enzyme whose amino acid sequence is SEQ ID NO:1, in which the amino acid at position 92 is replaced by a Serine (S), the amino acid at position 13 is replaced by an Arginine (R), the amino acid at position 123 is replaced by a Serine (S), the amino acid at position 91 is replaced by a Glutamine (Q) and the amino acid at position 157 is replaced by an Arginine (R), or A mutant enzyme whose amino acid sequence is SEQ ID NO:1, in which the amino acid at position 92 is replaced by a Glycine (G), the amino acid at position 93 is replaced by a Threonine (T), the amino acid at position 13 is replaced by a Glutamine (Q), the amino acid at position 123 is replaced by a Serine (S), the amino acid at position 91 is replaced by a Glutamine (Q) and the amino acid at position 157 is replaced by a Lysine (K), or A mutant enzyme whose amino acid sequence is SEQ ID NO:1, in which the amino acid at position 92 is replaced by a Glycine (G), the amino acid at position 93 is replaced by a Threonine (T), the amino acid at position 13 is replaced by an Arginine (R), the amino acid at position 123 is replaced by a Serine (S), the amino acid at position 91 is replaced by a Glutamine (Q) and the amino acid at position 157 is replaced by a Lysine (K), or A mutant enzyme whose amino acid sequence is SEQ ID NO:1, in which the amino acid at position 92 is replaced by a Glycine (G), the amino acid at position 93 is replaced by a Threonine (T), the amino acid at position 13 is replaced by a Glutamine (Q), the amino acid at position 123 is replaced by a Serine (S), the amino acid at position 91 is replaced by a Glutamine (Q) and the amino acid at position 157 is replaced by an Arginine (R), or A mutant enzyme whose amino acid sequence is SEQ ID NO:1, in which the amino acid at position 92 is replaced by a Glycine (G), the amino acid at position 93 is replaced by a Threonine (T), the amino acid at position 13 is replaced by an Arginine (R), the amino acid at position 123 is replaced by a Serine (S), the amino acid at position 91 is replaced by a Glutamine (Q) and the amino acid at position 157 is replaced by an Arginine (R).

In another embodiment, the mutant enzyme of the invention may comprise the four above-mentioned mutations (1) to (4), in addition to in addition to 92G/93P, or 92G/93S, or 92G/93G.

In this case the mutant enzyme of the invention can have the amino acid sequence SEQ ID NO:38, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Proline (P), the amino acid at position 91 is replaced by a Glutamine (Q), and the amino acid at position 157 is replaced by a Lysine (K).

The mutant enzyme of the invention can also have the amino acid sequence SEQ ID NO:39, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Glycine (G), the amino acid at position 91 is replaced by a Glutamine (Q), and the amino acid at position 157 is replaced by a Lysine (K).

The mutant enzyme of the invention can also have the amino acid sequence SEQ ID NO:40, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Serine (S), the amino acid at position 91 is replaced by a Glutamine (Q), and the amino acid at position 157 is replaced by a Lysine (K).

The mutant enzyme of the invention can also have the amino acid sequence SEQ ID NO:41, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Proline (P), the amino acid at position 91 is replaced by a Glutamine (Q), and the amino acid at position 157 is replaced by an Arginine (R).

The mutant enzyme of the invention can also have the amino acid sequence SEQ ID NO:42, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Glycine (G), the amino acid at position 91 is replaced by a Glutamine (Q), and the amino acid at position 157 is replaced by an Arginine (R).

Alternatively, the mutant enzyme of the invention can also have the amino acid sequence SEQ ID NO:43, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Serine (S), the amino acid at position 91 is replaced by a Glutamine (Q) and the amino acid at position 157 is replaced by an Arginine (R).

The present invention also targets:

A mutant enzyme whose amino acid sequence is SEQ ID NO:1, in which the amino acid at position 92 is replaced by a Glycine (G), the amino acid at position 93 is replaced by a Proline (P), the amino acid at position 13 is replaced by a Glutamine (Q), the amino acid at position 123 is replaced by a Serine (S), the amino acid at position 91 is replaced by a Glutamine (Q) and the amino acid at position 157 is replaced by a Lysine (K), or A mutant enzyme whose amino acid sequence is SEQ ID NO:1, in which the amino acid at position 92 is replaced by a Glycine (G), the amino acid at position 93 is replaced by a Serine (S), the amino acid at position 13 is replaced by a Glutamine (Q), the amino acid at position 123 is replaced by a Serine (S), the amino acid at position 91 is replaced by a Glutamine (Q) and the amino acid at position 157 is replaced by a Lysine (K), or A mutant enzyme whose amino acid sequence is SEQ ID NO:1, in which the amino acid at position 92 is replaced by a Glycine (G), the amino acid at position 93 is replaced by a Glycine (G), the amino acid at position 13 is replaced by a Glutamine (Q), the amino acid at position 123 is replaced by a Serine (S), the amino acid at position 91 is replaced by a Glutamine (Q) and the amino acid at position 157 is replaced by a Lysine (K), or A mutant enzyme whose amino acid sequence is SEQ ID NO:1, in which the amino acid at position 92 is replaced by a Glycine (G), the amino acid at position 93 is replaced by a Proline (P), the amino acid at position 13 is replaced by an Arginine (R), the amino acid at position 123 is replaced by a Serine (S), the amino acid at position 91 is replaced by a Glutamine (Q) and the amino acid at position 157 is replaced by a Lysine (K), or A mutant enzyme whose amino acid sequence is SEQ ID NO:1, in which the amino acid at position 92 is replaced by a Glycine (G), the amino acid at position 93 is replaced by a Serine (S), the amino acid at position 13 is replaced by an Arginine (R), the amino acid at position 123 is replaced by a Serine (S), the amino acid at position 91 is replaced by a Glutamine (Q) and the amino acid at position 157 is replaced by a Lysine (K), or A mutant enzyme whose amino acid sequence is SEQ ID NO:1, in which the amino acid at position 92 is replaced by a Glycine (G), the amino acid at position 93 is replaced by a Glycine (G), the amino acid at position 13 is replaced by an Arginine (R), the amino acid at position 123 is replaced by a Serine (S), the amino acid at position 91 is replaced by a Glutamine (Q) and the amino acid at position 157 is replaced by a Lysine (K), or A mutant enzyme whose amino acid sequence is SEQ ID NO:1, in which the amino acid at position 92 is replaced by a Glycine (G), the amino acid at position 93 is replaced by a Proline (P), the amino acid at position 13 is replaced by a Glutamine (Q), the amino acid at position 123 is replaced by a Serine (S), the amino acid at position 91 is replaced by a Glutamine (Q) and the amino acid at position 157 is replaced by an Arginine (R), or A mutant enzyme whose amino acid sequence is SEQ ID NO:1, in which the amino acid at position 92 is replaced by a Glycine (G), the amino acid at position 93 is replaced by a Serine (S), the amino acid at position 13 is replaced by a Glutamine (Q), the amino acid at position 123 is replaced by a Serine (S), the amino acid at position 91 is replaced by a Glutamine (Q) and the amino acid at position 157 is replaced by an Arginine (R), or A mutant enzyme whose amino acid sequence is SEQ ID NO:1, in which the amino acid at position 92 is replaced by a Glycine (G), the amino acid at position 93 is replaced by a Glycine (G), the amino acid at position 13 is replaced by a Glutamine (Q), the amino acid at position 123 is replaced by a Serine (S), the amino acid at position 91 is replaced by a Glutamine (Q) and the amino acid at position 157 is replaced by an Arginine (R), or A mutant enzyme whose amino acid sequence is SEQ ID NO:1, in which the amino acid at position 92 is replaced by a Glycine (G), the amino acid at position 93 is replaced by a Proline (P), the amino acid at position 13 is replaced by an Arginine (R), the amino acid at position 123 is replaced by a Serine (S), the amino acid at position 91 is replaced by a Glutamine (Q) and the amino acid at position 157 is replaced by an Arginine (R), or A mutant enzyme whose amino acid sequence is SEQ ID NO:1, in which the amino acid at position 92 is replaced by a Glycine (G), the amino acid at position 93 is replaced by a Serine (S), the amino acid at position 13 is replaced by an Arginine (R), the amino acid at position 123 is replaced by a Serine (S), the amino acid at position 91 is replaced by a Glutamine (Q) and the amino acid at position 157 is replaced by an Arginine (R), or A mutant enzyme whose amino acid sequence is SEQ ID NO:1, in which the amino acid at position 92 is replaced by a Glycine (G), the amino acid at position 93 is replaced by a Glycine (G), the amino acid at position 13 is replaced by an Arginine (R), the amino acid at position 123 is replaced by a Serine (S), the amino acid at position 91 is replaced by a Glutamine (Q) and the amino acid at position 157 is replaced by an Arginine (R).

The present invention also targets all mutant enzymes containing 92S or 92G/93T, optionally also containing at least one, preferably two, preferably three and more preferably four of the above-mentioned mutations (1) to (4), and containing any other mutations that do not affect their phosphodeoxyribosyltransferase activity. The present invention further targets all mutant enzymes containing 92G/93P, or 92G/93S, or 92G/93G, optionally also containing at least one, preferably two, preferably three and more preferably four of the above-mentioned mutations (1) to (4), and containing any other mutations that do not affect their phosphodeoxyribosyltransferase activity. Such mutations are numerous and can be easily inferred by the skilled person in view of the amino acid sequence and the three dimensional conformation of the mutant enzymes of the invention.

In particular, the present invention targets all mutant enzymes containing 92S or 92G/93T, optionally also containing at least one, preferably two, preferably three and more preferably four of the above-mentioned mutations (1) to (4), and which are homologous to the mutant enzymes described in the present invention. In another embodiment, the present invention targets all mutant enzymes containing 92G/93P, or 92G/93S, or 92G/93G, optionally also containing at least one, preferably two, preferably three and more preferably four of the above-mentioned mutations (1) to (4), and which are homologous to the mutant enzymes described in the present invention.

In the context of the invention, two amino acid sequences are "homologous" when at least about 80%, alternatively at least about 81%, alternatively at least about 82%, alternatively at least about 83%, alternatively at least about 84%, alternatively at least about 85%, alternatively at least about 86%, alternatively at least about 87%, alternatively at least about 88%, alternatively at least about 89%, alternatively at least about 90%, alternatively at least about 91%, alternatively at least about 92%, alternatively at least about 93%, alternatively at least about 94%, alternatively at least about 95%, alternatively at least about 96%, alternatively at least about 97%, alternatively at least about 98%, alternatively at least about 99% of their amino acids are identical, and provided that they have a significant mono, di or tri-phosphodeoxyribosyltransferase activity. Preferably the homologous sequences are identified by using the algorithm of Needleman and Wunsch.

Mono, di or tri-phosphodeoxyribosyltransferase activity can be assessed as disclosed in the experimental part of the invention, that is, briefly, by i) contacting the said mutant enzyme with a mono-phosphate dexoyribosyl nucleoside (dNMP), a di-phosphate dexoyribosyl nucleoside (dNDP) or a tri-phosphate dexoyribosyl nucleoside (dNTP) and a second base or an analog thereof in appropriate conditions and ii) by measuring the formation of the desired nucleoside due to the transfer of the mono-, di- or tri-phosphate deoxyribose on a base or an analog thereof.

In another aspect, the present invention also targets a polynucleotide encoding a mutant enzyme as defined above.

As used herein, the term "polynucleotide" designates any nucleotide sequence, either naturally-occurring or genetically obtained. It is for example DNA (deoxyribonucleic acid) or RNA (ribonucleic acid). As used herein, a nucleotide sequence "encodes" a protein if when expressed, it results in the production of that protein; i.e., it "encodes" the amino acid sequence of that protein.

In a preferred embodiment, the sequence of the polynucleotide of the invention is chosen among SEQ ID NO: 24 to 31 (encoding SEQ ID NO:3 to 10 respectively), that have been generated by the present inventors. According to the invention, the sequence of the polynucleotide of the invention can further be chosen among SEQ ID NO: 44 to 49 (encoding SEQ ID NO:38 to 43 respectively). The present invention also concerns any polynucleotide whose sequence is homologous to SEQ ID NO: 24 to 31 or SEQ ID NO: 44 to 49 but, due to codon degeneracy, does not contain precisely the same nucleotide sequence. By "homologous", it is herein meant that the sequences encodes the same proteins but, due to codon degeneracy, are not identical.

The polynucleotide of the invention may be found or integrated in any cloning and/or expression vector known in the art, said vector being for example useful for ensuring its propagation in a host cell, or for ensuring its expression. The recombinant DNA technologies used to construct the cloning and/or expression vector of the invention are well-known to those skilled in the art. Standard techniques are used for cloning, DNA isolation, amplification and purification; enzymatic reactions involving DNA ligase, DNA polymerase, restriction endonucleases are performed following the manufacturer's instructions. These techniques are generally conducted in accordance with Sambrook et al, 1989. The cloning and/or expression vectors targeted in the present invention include plasmids, cosmids, bacteriophages, retroviruses and other animal viruses, artificial chromosomes such as YAC, BAC, HAC and other similar vectors.

In a third aspect, the present invention therefore targets a cloning and/or an expression vector (hereafter designated as "recombinant vector") comprising the polynucleotide of the invention.

The term "vector" herein means the vehicle by which a DNA or RNA sequence of a foreign gene can be introduced into a recombinant cell so as to transform it and promote expression of the introduced sequence. Vectors may include for example, plasmids, phages, and viruses and are discussed in greater detail below. Indeed, any type of plasmid, cosmid, YAC or viral vector may be used to prepare a recombinant nucleic acid construct which can be introduced to a recombinant cell where expression of the protein of interest is desired. Alternatively, wherein expression of the mutant enzyme is desired in a particular type of cell, viral vectors that selectively infect the desired cell type or tissue type can be used. For example, viral vectors, such as lentiviruses, retroviruses, herpes viruses, adenoviruses, adeno-associated viruses, vaccinia virus, baculovirus, and other recombinant viruses with desirable cellular tropism. Methods for constructing and using viral vectors are known in the art (see, Miller and Rosman, *BioTechniques*, 1992).

In a preferred embodiment, said recombinant vector is a viral vector, a plasmid or a naked DNA.

In another preferred embodiment, the said recombinant vector contains an efficient promoter which is operatively linked to—and controls the expression of—the polynucleotide sequence of the invention. As used herein, a "promoter" is a sequence of nucleotides from which transcription may be initiated of DNA operably linked downstream (i.e. in the 3' direction on the sense strand of double-stranded DNA). Within the promoter sequence will be found a transcription initiation site (conveniently found, for example, by mapping with nuclease S1), as well as protein binding domains (consensus sequences) responsible for the binding of RNA polymerase. Promoters which may be used to control gene expression in the context of the present invention are for example the ones that are functional in non-vertebrate cells or in vertebrate cells.

Promoters suitable for constitutive expression in mammalian cells include the cytomegalovirus (CMV) immediate early promoter, the adenovirus major late promoter, the phosphoglycero kinase (PGK) promoter, and the thymidine kinase (TK) promoter of herpes simplex virus (HSV)-1, the elongation factor 1 alpha (EF1alpha) promoter, the Rous Sarcoma Virus (RSV) promoter, and long terminal repeats (LTR) retroviral promoters. Inducible eukaryotic promoters regulated by exogenously supplied compounds, include without limitation, the zinc-inducible metallothionein (MT) promoter, the dexamethasone (Dex)-inducible mouse mammary tumor virus (MMTV) promoter, the T7 polymerase promoter system (WO 98/10088), the ecdysone insect promoter, the tetracycline-repressible promoter, the tetracycline-inducible promoter, the RU486-inducible promoter and the rapamycin-inducible promoter. For example, for non-vertebrate cells, the regulatory sequences of the metallothionein gene can be used (Brinster et al., *Nature,* 296: 39-42, 1982).

In a fourth aspect, the present invention also targets a non-human recombinant cell containing the polynucleotide of the invention, or the recombinant vector of the invention. This recombinant cell can be any cell provided that it is not a human embryonic stem cell or a human germinal cell. In particular, in the context of the present invention, "recombinant" cells are any cells which can be used for producing recombinant proteins, such as "non-vertebrate" (or invertebrate) cells, vertebrate cells, plant cells, yeast cells, or prokaryote cells. They are preferably non-vertebrate, prokaryote or vertebrate cells.

In the context of the invention, non-vertebrate cells are preferably insect cells, such as *Drosophila* or Mosquito cells, more preferably *Drosophila* S2 cells. In the context of the invention, vertebrate cells are preferably EBX, CHO, YB2/O, COS, HEK, NIH3T3 cells or derivatives thereof. Prokaryote cells which can be used in the context of the invention are typically *E. Coli* bacteria or *Bacillus Subtilis* bacteria.

Consequently, the recombinant vector of the invention contains a promoter which is efficient in said recombinant cell. The skilled person well-knows which promoter can be used for each kind of cell.

Methods for generating recombinant cells are well-known. Some of them are described in EP1692281 and are incorporated herein by reference. Briefly, the recombinant transgene containing the sequence of the mutant enzyme of the invention, optionally contained in a linearized or non-linearized vector, or in the form of a vector fragment, are inserted in a host cell using microinjection into the nucleus (U.S. Pat. No. 4,873,191), transfection by calcium phosphate precipitation, lipofection, electroporation, transformation with cationic polymers (PEG, polybrene, DEAE-Dextran) or viral infection.

In a fifth aspect, the present invention also targets a method for producing the mutant enzyme of the invention, said method comprising the steps of:

a) culturing the recombinant cell of the invention in appropriate conditions so as to allow the production of the protein(s) encoded by the recombinant vector contained in said recombinant cell, b) collecting the mutant enzyme which is expressed from the cell culture.

"Appropriate conditions" for allowing the production of proteins encoded by a recombinant vector are well-known in the art and do not need to be detailed further. They obviously depend on the nature of the recombinant cell (mammalian, bacterial, or insect cell), on the kind of promoter which is used (inducible or not), etc.

One exemplary protocol for producing the mutant enzyme of the invention is disclosed in the experimental part below. Briefly, plasmids containing the sequence of the mutant enzyme of the invention were used to transform *E. Coli* bacterial strain BLi5 suspended in YT medium. These cells were grown under agitation at 37° C. until $OD_{600}$=0.6, after what isopropyl-1-thio-βD-galacto-pyranoside was added to a final concentration of 1 mM, and the cultures were incubated for 2.5 h. Cells were resuspended in MES 50 mM at pH6.0 and broken by one passage through a French press at 14000 p.s.i. Cell debris were pelleted by centrifugation, preferably at 12000 rpm for 20 min at 4° C. The total proteins contained in the supernatant were separated by an anion exchange chromatography with a linear NaCl gradient in MES 50 mM pH6.0. Fractions containing the enzymes were pooled and precipitated at 4° C. by adding solid ammonium sulfate. The precipitate was pelleted by centrifugation, preferably at 12000 rpm for 20 min at 4° C. Pellet was finally resuspended into MES 50 mM/NaCl 100 mM (pH 6.0) and purified on a column.

Use of the Enzyme Mutants of the Invention

As mentioned previously, the present inventors identified new enzymes that are able to transfer 5'-phosphorylated deoxyribose between a phosphated deoxyribonucleotide (dN-P) and a nucleobase (N'), according to the following formula I:

$$dN\text{-}(P)_x + N' \leftrightharpoons N + dN'\text{-}(P)_x$$

where 'x' stands for 0, 1, 2 or 3. These enzymes are not substrate-specific as they are able to transfer said deoxyribose moiety on any acceptor nucleobase (A, T, G, or C), would it be canonical or not (analogs). Moreover, these enzymes have advantageous mono-, di-, and triphosphodeoxyribosyltransferase activities. They are therefore very promising tools for synthesizing various deoxyribonucleotide tri-phosphate (dNTPs) or analogs thereof. The use of these enzymes therefore opens the road to new synthetic pathways of deoxyribonucleotides.

As disclosed in the experimental part below, the present inventors have observed promising transferase activity for the eight enzyme mutants SEQ ID NO:3 (PDTM1), SEQ ID NO:4 (PDTM2), SEQ ID NO:5 (PDTM3), SEQ ID NO:6 (PDTM4), SEQ ID NO:7 (PDTM5), SEQ ID NO:8 (PDTT0), SEQ ID NO:9 (PDTT1) and SEQ ID NO:10 (PDTT2) with different deoxynucleotides donors and bases as acceptors (see experimental part below, in particular table 4). More precisely, it is to note that all these mutants are able to transfer deoxyribose 5-monophosphate between cytosine or adenine and analogs of natural bases such as 5-fluorouracil, 5-bromouracil, 2,6-diaminopurine, 6-chloropurine, and 2,6-dichloropurine.

Moreover, it is noteworthy that all the mutants carrying the 92G/93T mutations, and especially SEQ ID NO:8 (PDTT0), SEQ ID NO:9 (PDTT1) and SEQ ID NO:10 (PDTT2) are able to transfer deoxyribose 5-biphosphate and deoxyribose 5-triphosphate between cytosine or adenine and analogs of natural bases such as 5-fluorouracil, 5-bromouracil, 2,6-diaminopurine, 6-chloropurine, and 2,6-dichloropurine.

Finally, the inventors have surprisingly found that the mutants carrying the 92G/93P or 92G/93G or 92G/93S mutations present similar catalytic properties as the mutants carrying the 92G/93T mutations. Notably, the mutants carrying the 92G/93P or 92G/93G or 92G/93S mutations are able to transfer deoxyribose 5-triphosphate between cytosine or adenine with interesting catalytic activities.

It can therefore be concluded that the mutant enzymes of the invention are useful to transfer deoxyribose 5-monophosphate, deoxyribose 5-diphosphate, deoxyribose 5-triphosphate or deoxyribose 5-1-thiotriphosphate on natural nucleobases and/or analogs thereof.

All the natural nucleobases can be modified by the mutant enzymes of the invention. However, the transfer of the phosphodeoxyribosyl moiety is weaker if the donor deoxyribonucleotide and the acceptor nucleobase are both purines or pyrimidines. This observation is in agreement with previous observations showing that the deoxyribose 5-phosphate transfer activity of NDT between purine bases is low, in particular when hypoxanthine is the acceptor bass (Kaminski P. A., *J. Biol. Chem.* 2002).

Of note, the transfer of the phosphodeoxyribosyl moiety is stronger between a deoxyribonucleotide and a nucleobase analog. As used herein, the terms "nucleoside analog" and "nucleobase analog" designate all the analogs that are known in the art. These analogs are well-known in the art. They are for example araC, gemcitabine, fludarabine, cladribine, clofarabine, troxacitabine, 5-fluorouracil, 5-bromouracil, 2,6-diaminopurine, 6-chloropurine, and 2,6-dichloropurine. More generally, all the analogs that are modified by the wild type NDT enzyme will be efficiently modified by the mutants of the invention. The analogs that are for example modified by the mutant enzymes of the invention are: 5-fluorouracil, 5-bromouracil, 2,6-diaminopurine, 6-chloropurine, and/or 2,6-dichloropurine, as shown in the experimental part below.

The utility of such enzymes is multiple: as tools for chemists to modify and/or synthesize deoxynucleotides enzymatically; for geneticists to manipulate genomes by controlled mutagenesis; for synthetic biologists to incorporate unnatural deoxynucleotides in vitro and in vivo.

The enzyme mutants of the invention can therefore be used in two main applications:
1) for in vitro synthesis of various deoxyribonucleotides, nucleobases or analogs thereof, for example in academic research and medical diagnosis.

These synthetic deoxyribonucleotides, nucleobases or analogs thereof can be further used for in vitro DNA mutagenesis, DNA labeling, or studying nucleotide metabolic enzymes.

As used herein, the term "nucleobase" designates either a purine nucleobase (Adenine A, Guanine G, or Purine analog) or a pyrimidine nucleobase (Uracil U, Thymine T, Cytosine C, or a Pyrimidine analog). These compounds are well-known in the art and do not need to be detailed in the present application.

As used herein, the term "deoxyribonucleotide" designates the monomer of DNA containing three parts: a nitrogenous base, a deoxyribose sugar, and one phosphate group. The nitrogenous base is bond to the 1' carbon of the deoxyribose, which is distinguished from ribose by the presence of a proton on the 2' carbon rather than an —OH group. The phosphate groups bind to the 5' carbon of the sugar. The three kinds of deoxyribonucleotide can be used by the mutant(s) of the invention: the deoxyribonucleotide monophosphate (currently known as dAMP, dGMP, dTMP, dUMP and dCMP), the deoxyribonucleotide diphosphate (currently known as dADP, dGDP, dTDP, dUDP and dCDP), and the deoxyribonucleotide triphosphate (currently known as dATP, dGTP, dTTP, dUTP and dCTP).

However, in a preferred embodiment, the present invention targets the use of the mutant enzyme of the invention for transferring a deoxyribose tri-phosphate moiety from a deoxyribonucleotide triphosphate.

As disclosed previously, the transfer of the phosphodeoxyribosyl moiety is weaker if the donor deoxyribonucleotide and the acceptor nucleobase are both purines or pyrimidines. Therefore, in a more preferred embodiment, when the donor deoxyribonucleotide is a purine, then the acceptor nucleobase or analog thereof is not a purine. In another preferred embodiment, when the donor deoxyribonucleotide is a pyrimidine, then the acceptor nucleobase or analog thereof is not a pyrimidine.

Preferred analogs useful in the present invention are chosen in the group consisting of: 5-fluorouracil, 5-bromouracil, 2,6-diaminopurine, 6-chloropurine, and/or 2,6-dichloropurine.

The present invention also targets a method for in vitro synthetizing various deoxyribonucleotides, nucleobases or analogs thereof, said method using the enzyme mutant(s) of the invention.

2) for in vivo synthesis of cytotoxic analogs that can be used as antibiotics, antiviral and anticancer agents.

As a matter of fact, the transfer of the mutant enzymes of the invention in highly proliferating cells such as tumor cells can trigger the in vivo generation of non-natural nucleosides or analogs, which are cytotoxic once incorporated in DNA. It is to note that deoxynucleoside analogues such as araC, gemcitabine, fludarabine, cladribine, clofarabine, and troxacitabine are already widely used in the treatment of hematological malignancies and solid tumors (cf. Hebrard C., et al, *Cancer Gene Therapy* 2009).

Consequently, the use the phosphodeoxyribosyltransferases reported here is a promising approach to deliver cytotoxic nucleotides in cancer cells (see Dm-dNK a multisubstrate enzyme with a high specific activity and a broad substrate specificity, which is an interesting candidate for suicide gene therapy in cancer, Munch-Petersen B., *J. Biol. Chem.* 1998).

The present invention also targets a method for in vivo synthetizing cytotoxic analogs that can be used as antibiotics, antiviral and anticancer agents, said method using the enzyme mutant(s) of the invention.

In a particular embodiment, the present invention targets an enzyme mutant as defined above, for use to transfer in vivo deoxyribose phosphate moiety between natural deoxyribonucleotides and nucleobases or analogs thereof.

All the terms "deoxyribonucleotides", "nucleobases" or "analogs" have been described above.

The enzyme mutants of the invention are delivered in vivo, i.e., in the cells of the individual (animal or human), by conventional means such as gene therapy, transfection, electroporation, etc. Vectors which can be used for gene therapy are well-known in the art. They are for example lentivirus, retrovirus, adenovirus, poxvirus, herpes virus, measle virus, foamy virus or adeno-associated virus (AAV). Viral vectors can be replication-competent, or can be genetically disabled so as to be replication-defective or replication-impaired.

Also, the present invention targets an enzyme mutant as defined above, for use for treating subjects suffering from cancer. In other words, the present invention targets the use of the mutant enzyme of the invention for manufacturing a medicament intended to treat subjects suffering from cancer. Said cancer is preferably a cancer with an upregulation of the Rcl enzyme, such as a human prostate cancer, breast cancers, and chronic lymphocyte leukemia for example. More generally, said medicament is useful for treating hematological cancers or solid tumors.

The invention also targets a therapeutical or a pharmaceutical composition containing, as active principle, at least one of the mutant enzyme of the invention in an effective amount. This pharmaceutical composition may also contain the recombinant vector or the recombinant cell of the invention, or any combination thereof.

An "effective amount" herein refers to an amount that is effective, at dosages and for periods of time necessary, to achieve the desired result, i.e., to treat effectively the patient suffering from cancer. An effective amount as meant herein should also not have any toxic or detrimental severe effects.

The said composition can also contain a pharmaceutically acceptable vehicle. By "pharmaceutically acceptable vehicle", it is herein designated any and all solvents, buffers, salt solutions, dispersion media, coatings, antibacterial and antifungal agents, isotonic and absorption delaying agents, and the like that are physiologically compatible. The type of carrier can be selected based upon the intended route of administration. In various embodiments, the carrier is suitable for intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of media and agents for pharmaceutically active substances is well known in the art.

The present invention also targets a method for treating cancer in a subject in need thereof, comprising the step of administering to said patient the pharmaceutical composition of the invention.

Kit of the Invention

In a final aspect, the present invention targets a kit containing:
- at least one of the mutant enzyme of the invention as described above,
- the polynucleotide of the invention, as described above, or
- the recombinant vector of the invention, as described above.

This kit is used advantageously for implementing the methods of the invention, as disclosed above.

Said kit may also contain mono-phosphate dexoyribosyl nucleosides (dNMP), di-phosphate dexoyribosyl nucleosides (dNDP) and/or a tri-phosphate dexoyribosyl nucleosides (dNTP), pooled in one recipient or separated in different recipient so as to perform in vitro or in vivo DNA synthesis.

It may finally contain instructions for implementing the method(s) of the invention.

Examples

Material and Methods

1. Chemicals

All chemicals were obtained from Aldrich/Sigma (except dCTPaS from Biolog).

2. List of the Oligonucleotides Used

```
F13R:
                                      (SEQ ID NO: 11)
CTTCGGTGCCGGCTGGCGCACTGACCGCCAAAAC

F13Q:
                                      (SEQ ID NO: 12)
CTTCGGTGCCGGCTGGCAGACTGACCGCCAAAACA

F13Qbis:
                                      (SEQ ID NO: 13)
TGTTTTGGCGGTCAGTCTGCCAGCCGGCACCGAAG D92S:
                                      (SEQ ID NO: 14)
ATCCCTGACGAAGAAAGCGTCGGCCTGGGCATG N123S:
                                      (SEQ ID NO: 15)
CTACGGCAAGCCGATCAGCCTCATGAGCTGGGGCG N123Sbis:
                                      (SEQ ID NO: 16)
CGCCCCAGCTCATGAGGCTGATCGGCTTGCCGTAG N123T:
                                      (SEQ ID NO: 17)
CTACGGCAAGCCGATCACCCTCATGAGCTGGGGCG N123Tbis:
                                      (SEQ ID NO: 18)
CGCCCCAGCTCATGAGGGTGATCGGCTTGCCGTAG -continued
E91Q:
                                      (SEQ ID NO: 19)
TGTCTACATCCCTGACGAACAGGGCACCGGCC E91Qbis:
                                      (SEQ ID NO: 20)
GGCCGGTGCCCTGTTCGTCAGGGATGTAGACA Y157K:
                                      (SEQ ID NO: 21)
GCAAGCTTTTACTTTACGGCACCTTCGTAGAAGTCGAAGC G92T93:
                                      (SEQ ID NO: 22)
GTCTACATCCCTGACGAAGAAGGCACCGGCCTGGGCA G92T93bis:
                                      (SEQ ID NO: 23)
TGCCCAGGCCGGTGCCTTCTTCGTCAGGGATGTAGAC
```

3. Construction of the Different Variants

Variant F13R was obtained by using plasmid pET24a NDT (SEQ ID NO: 32) as DNA template and oligonucleotide F13R (SEQ ID NO:11) using the QuikChange® Multi site-directed Mutagenesis kit (Stratagene) according to the manufacturing protocol.

Variants S92 and R13 S92 were obtained by using plasmid pET24a NDT as DNA template and oligonucleotides D92S and D92S and F13R respectively using the QuikChange® Multi site-directed Mutagenesis kit (Stratagene) according to the manufacturing protocol.

Variants S92 S123, R13 S92 S123, R13 S92 T123, R13 G92 T93 S123, R13 Q91 G92 T93 S123, Q13 S92 S123 and Q13 Q91 S92 S123:

Oligonucleotides: N123S-, N123T-, G92 T93-, E91Q-, F13Q-, E91Q- and T7 prom (SEQ ID NO:33); N123S, N123T, G92 T93, E91Q, F13Q, E91Q and T7 term (SEQ ID NO:34) were used in two separate PCR reactions using plasmids pET24a NDT S92, pET24a NDT R13 S92, pET24a NDT R13 S92 S123, pET24a NDT R13 G92 T93 S123, pET24a NDT S92 S123 and pET24a NDT Q13 S92 S123 as DNA templates respectively. The parameters used 1 cycle of 5 min at 95° C.; 25 cycles of 30 s at 95° C., 30 s at 53° C., and 30 sec at 72° C.; and 1 cycle of 10 min at 72° C. The annealing temperature was dependent on the pairs of oligonucleotides used. Oligonucleotides T7prom and T7term were used in a second PCR using aliquots of the first one using the same parameters as above with the exception of an annealing temperature of 61° C.

Variant R13 G92 T93 S123 K157:

Oligonucleotides T7 prom and Y157K were used in a standard PCR reaction using plasmid pET24a NDT R13 G92 T93 S123 as DNA template.

The amplified DNA fragments were purified by using the QIAquick PCR purification kit (Qiagen) and then digested with NdeI and BamHI enzymes over 2 h at 37° C. and repurified. Each PCR product was ligated with plasmid pET24a that had been digested with the same restriction enzymes. The ligation mixtures were used to transform strain DH5a.

Plasmids with the correct sequence were used to transform strain BLi5.

Variant Q13 Q91 S92 S123:

Oligonucleotides T7 prom/E91Q and T7 term/E91Qbis were used in a standard PCR reaction using plasmid pET24a NDT Q13 S92 S123 as DNA template. 0.5 µL of each PCR product has been used in a second PCR reaction using oligonucleotides T7 prom et T7 term. The amplified DNA fragments were purified by using the QIAquick PCR purification kit (Qiagen) and then digested with NdeI and BamHI enzymes over 2 h at 37° C. and repurified. Each PCR product was ligated with plasmid pET24a that had been digested with the same restriction enzymes. The ligation mixtures were used to transform strain DH5a.

Plasmids with the correct sequence were used to transform strain BLi5.

Further variants were generated by adapting this protocol in order to other mutations of the invention herein described, according to conventional methods well-known by the person skilled in the art.

4. Overexpression and Purification

Plasmids containing an insert of the correct size were sequenced at the "Plateforme Génomique PF1", Institut Pasteur. Those with the correct sequences were used to transform strain BLi5.

650 ml of 2×YT medium inoculated with an overnight culture of BLi5 containing any of the pET24a+PDT* was grown under agitation at 37° C. until $OD_{600}$=0.6. Isopropyl-1-thio-βD-galacto-pyranoside was added to a final concentration of 1 mM, and the cultures were incubated for 2.5 h. Bacteria were centrifuged, and the pellets were frozen at −20° C. Cells were resuspended in 20 ml of MES 50 mM pH6.0 and broken by one passage through a French press at 14000 p.s.i. Cell debris were pelleted by centrifugation at 12000 rpm for 20 min at 4° C. The total proteins contained in the supernatant were separated by an anion exchange chromatography on a Hi Trap Q HP with a linear gradient from 0 to 300 mM NaCl gradient in MES 50 mM pH6.0 at 2 ml min' for 100 min. Fractions containing the enzyme were pooled and precipitated at 4° C. by adding solid ammonium sulfate (0.6 mg/ml). The precipitate was pelleted by centrifugation at 12000 rpm for 20 min at 4° C. Pellet was resuspended into MES 50 mM NaCl 100 mM pH 6.0 and purified on a Hi Load Superdex S200 column at 1 ml min$^{-1}$. The purified proteins ran as a single band at approximately 18 kDa, consistent with the predicted molecular weight and was >98% pure as judged by SDS-PAGE with Coomassie Blue staining. Protein concentration was determined spectrophotometrically by UV absorption at 280 nm using an $\epsilon_{280}$=34380.

5. Enzyme Assay

The standard assay ("first protocol for enzyme assay") for the different NDTs consisted of 5-15 μg of NDT in 50 mM MES buffer pH 6.0, dNxP (dNMP, or dNDP or dNTP) 3 mM and a base 1 mM in a total volume of 50 μL. Assays were incubated for 60 min at 37° C. The products of the reactions were analyzed each 7 min by Rapid resolution high performance liquid chromatography using a reverse-phase column (ZORBAX Eclipse XDB-C18 2.1*50 mm 1.8 μM) with a flow rate of 0.25 ml/min and a linear gradient of 1-12% $CH_3CN$ (2-25% $CH_3CN$ or 1-90% $CH_3CN$) in 20 mM triethylammonium acetate, pH 7.5, buffer for 7 min. The low resolution mass spectra of the newly synthesized deoxyribonucleotides were obtained on an Agilent 1200 series LC/MS 6120 quadrupole system using an atmospheric electrospray ionization system.

In specific cases, an alternative protocol was used to perform the enzyme assay. In this second protocol, the dNxP (dNMP, or dNDP or dNTP) concentration was of only 2 mM, instead of 3 mM. All of the other conditions were identical to those of the first protocol.

Unless specifically mentioned, the results presented hereafter have been obtained by using the first protocol for performing the enzyme assay.

6. Crystallization and X-Ray Data Collection

Crystal growth conditions were screened using Cations, Anions and AmSO4 kits from Qiagen. Crystallization was then optimised in medium concentration of $NH_4SO_4$ (~1.2 M) in 0.1 M HEPES at pH 7.7, in the presence of glycerol and/or small PEGs (e.g.: PEG400 2%). Co-crystallization with ATP or CMP were also attempted. X-ray diffraction data sets were collected from frozen single crystals at the European Synchrotron Radiation Facility (Grenoble, France, beamline ID23-2) and processed with the programs MOSFLM, SCALA, and TRUNCATE from the CCP4 program suite (Table 1).

The structure was solved by molecular replacement using the program MolRep and the crystal structure of the wild-type NDT from *Lactobacillus leichmannii* (PDB1F8Y) as a search model. Two crystal forms were obtained both in the 1213 trigonal space group but only the one with the larger cell (a=b=c=218.5 Å versus 151.3 Å) diffracted well. The structure of PDTT2 was solved at 2.7 Å and refined using the program COOT and the program REFMAC5, using a translation/liberation/screw model (Table 1).

Results

1. Structure Guided Design of a Monophosphodeoxyribosyltransferase

An hypothetical common ancestor to Rcl and NDT was reconstructed by phylogenetic means using the software PAML 4.3 (PMID:17483113). The resurrected proteins being poorly soluble and inactive (not shown), an alternative approach was to compare the sequences and structures of NDT and Rcl to create a chimera with the desired activities (i.e., a deoxyribosyltransferase activity with the broadest substrate specificity).

NDT was chosen as a starting template as its transferase activity was more interesting from the synthetic point of view (since it exchanges deoxyribose between pyrimidines and purines, and vice versa, between two pyrimidines and to a lesser extent between two purines). Furthermore, it tolerates substitutions on the base. The idea was to keep intact the catalytic core while reshaping the substrate specificity.

First, two aminoacids, D92 and N123 of NDT, were substituted to neutral and smaller serines. In NDT, these aspartate and asparagine interact with the 5'-OH group of 5-methyl-2'-deoxypseudouridine (5mΨU) by forming hydrogen bonds and prevent entrance of a large and negatively charged phosphate group. At equivalent positions in the active site of Rcl, two serines (S87 and S117, respectively) are found (data not shown). These changes confer to the NDT single mutant D92S (hereafter PDTM1, for phosphodeoxyribosyltransferase monophosphate) and the double mutant D92S, N123S (the enzyme mutant called "PDTM2") the ability to transfer deoxyribose 5-phosphate between cytosine and adenine although with a low efficiency (see Table 2 below).

TABLE 1

Data collection and refinement statistics for PDTT2.

| | PDTT2 |
|---|---|
| Beamline | ID29 |
| Data collection | |
| Space group | I213 |
| Cell dimension | |
| a = b = c (Å) | 218.5 |
| No. molecules in a.u | 8 |
| Wavelength (Å) | 0.9793 |
| Resolution (Å)[1] | 2.68 |
| Rmerge (%)[1-2] | 9.0 |
| I/σI[1] | 10.9 |
| Completeness (%)[1] | 99.8 |

TABLE 1-continued

Data collection and refinement statistics for PDTT2.

| | PDTT2 |
|---|---|
| Redundancy[1] | 5.1 |
| B-wilson | 64.1 |
| Refinement | |
| Resolution (Å) | 2.69 |
| No. Reflections | 48494 |
| Rwork/Rfree (%)[3-4] | 19.8/24.9 |
| No. Protein Atoms | 10091 |
| No. Waters molecules | 213 |
| Ligand type | 14 SO4 + 9 PEG |
| B-factors (Å$^2$) | |
| Protein | 48.1 |
| Ligand (SO4/PEG) | 66.6/75.6 |
| Water | 44.8 |
| R.m.s deviations[5] | |
| Bond lengths (Å) | 0.10 |
| Bond angles (°) | 1.179 |

[1]Values in parentheses refer to the outermost resolution shell.
[2]Rmerge = Σhkl Σ I | Ihkl,i - Iaverage,hkl |/|ΣhklΣi|Ihkl,i|x100.
[3]Rwork = Σhkl|Fobs - Fcalc|/Σhkl |Fobs|x100.
[4]Rfree is calculated in the same way on a subset of reflections that are not used in the refinement (5%).
[5]Deviation from ideal values.

Overlay of the active sites of Rcl and NDT also predicts a steric clash between F13 and an incoming phosphate group (not shown). Upon, substitution of F13 to the positively charged arginine (to give the so-called "PDTM3" from PDTM1 or the so-called "PDTM4" from PDTM2), the deoxyribose 5-phosphate transferase activity between C and A is enhanced by a factor of 50. Finally, the F13 was also substituted by a polar but neutral glutamine (generating the enzyme mutant called "PDTM5") leading also to significant improvements in activity (see table 2 below). This improvement is mainly due to a better affinity for dCMP, the $K_m$ for dCMP varying from 22 mM (PDTM3) to 11 or 12 mM (PDTM4 and PDTM5 respectively) (see table 3 below).

Of note, the mutant carrying only the mutation F13R has been tested on the couples dCMP+A and dCMP+T but no deoxyribose 5-phosphate transferase activity was observed (data not shown).

The phosphodeoxyribosyltransferase activity is not restricted to cytosine as donor and to adenine as acceptor. PDTM3 is also able to transfer deoxyribose 5-phosphate between A and C, C and T but with a two-fold and 4 fold lower activity than between C and A. PDTM4 is two times more active than PDTM3 whatever the couple of bases tested. In contrast, PDTM5 transfers deoxyribose 5-phosphate efficiently between C and A and A and C but is much less active on both pyrimidine-pyrimidine and purine-purine transfer (see table 2 below).

TABLE 2

Specific activities of alignment based PDT variants in the presence of different purines and pyrimidines as donors and acceptors of deoxyribose 5-phosphate.

| Reactions [b] | Enzymes [a] | | | | | | | | |
|---|---|---|---|---|---|---|---|---|---|
| | NDTWT | PDTM1 | PDTM2 | PDTM3 | PDTM4 | PDTM5 | PDTT0 | PDTT1 | PDTT2 |
| dCMP + A ⇌ dAMP + C | 0.1 | 1.8 | 1.7 | 79.7 | 170 | 296 | 46.3 | 78 | 286 |
| dAMP + C ⇌ dCMP + A | | | | 34.7 | 77.6 | 206 | 23.7 | 5 | 31 |
| dCMP + T ⇌ dTMP + C | | | | 18.2 | 52 | 1.7 | <0.1 | <0.1 | 1.1 |
| dGMP + A ⇌ dAMP + G | | | | 8.5 | 57 | 81 | 49 | 32 | 50 |
| dAMP + Hx ⇌ dIMP + A | | | | 2 | <0.1 | <0.1 | <0.1 | <0.1 | <0.1 |
| dCDP + A ⇌ dADP + C | | | | | | | <0.1 | 31 | 66 |
| dADP + C ⇌ dCDP + A | | | | | | | | 12 | 8 |
| dCDP + U ⇌ dUDP + C [c] | | | | | | | | 6 | 8 |
| dGDP + A ⇌ dADP + G | | | | | | | | 15 | 33 |
| dADP + Hx ⇌ dIDP + A | | | | | | | | <0.1 | <0.1 |
| dCTP + A ⇌ dATP + C | | | | | | | <0.1 | 10 | 51 |
| dATP + C ⇌ dCTP + A | | | | | | | | 1 | 15 |
| dCTP + T ⇌ dTTP + C | | | | | | | | 1 | 1.4 |
| dGTP + A ⇌ dATP + G | | | | | | | | 25 | 36 |
| dATP + Hx ⇌ dITP + A | | | | | | | | <0.1 | <0.1 |

[a] NDT and PDT sequences are: NDT: F13E91D92V93N123Y157, PDTM1: S92, PDTM2: S92 S123, PDTM3: R13 S92, PDTM4: R13 S92 S123, PDTM5: Q13 S92 S123 PDTT0: R13 G92 T93 S123, PDTT1: R13 G92 T93 S123 K157 and PDTT2: R13 Q91 G92 T93 S123.
[b] The donor concentration was 3 mM and the acceptor 1 mM.
[c] U was used as acceptor base instead of T. Activities are expressed in nanomoles of deoxynucleotides synthesized per min per mg of protein Accommodation of the Phosphate Binding Site to Di- and Triphosphate Then it was aimed to build a larger phosphate binding site and to take advantage of the macrodipole of the central helix bearing the common catalytic glutamate (E98 in NDT) as observed in the Rcl-GMP complex. A more drastic reshaping of the active site was therefore attempted by replacing the two amino acids DV by GT at positions 92 to 93 (leading to the enzyme mutant called "PDTT0") in order to remove a negatively charged residue and simultaneously make the backbone amide groups more accessible to better accommodate a phosphate group. Subsequently, in the context of the variant PDTT0 ("PDTT" for "phosphodeoxyribosyltransferase triphosphate"), another positively charged residue was added (mutation Y157K; named "PDTT1") or a negative charge was removed (E91Q; named "PDTT2") so as to favor further the entrance of nucleotides.

In order to track possible structural rearrangements induce by the mutations; several variants (PDTM1, PDTM4, and PDTT2) were tested for crystallization. Crystals of the apo form of PDTM1 and PDTT2 were obtained and the structure solved by molecular replacement. The crystals of PDTM1 diffracted at best to 3.5 Å and the resulting structure appeared identical to the parent one and was not further refined. Conversely, the structure of PDTT2 was refined to 2.7 Å. This crystal possesses a large unit cell that is composed of one dimer and one biologically relevant hexamer. The dimer belongs to a similar hexamer thanks to the 3-fold crystallographic symmetry In this structure, the overall architecture is also very well conserved (not shown). However, the mutated loop 91-93 is either partially disordered or it adopts two distinct conformations. In one conformation (e.g.: chains A and B), a sulphate ion is bound at the dimeric interface involving mainly the loop 91-93. In an alternative conformation (e.g., chain G and H), the sulphate ion is observed within the substrate binding site of the modified NDT. The overlay of its active site with that of Rcl bound to GMP (Yang Y. et al, *J. Mol. Biol.* 2009) shows that this sulfate ion localized in close contact with the phosphate group of GMP. Consequently, it was further tested whether PDTT0-PDTT2 variants could accept diphosphate and triphosphate deoxyribonucleotide as substrates.

This hypothesis was confirmed by monitoring the specific activity, in the presence of dCDP or dCTP as donor and adenine as acceptor (see table 2 above). The kinetic parameters were determined for the best variants with dCMP, dCDP and dCTP as substrates, at a concentration of A being fixed (see table 3 below). The $K_m$ for adenine was between 80 and 160 µM when measured using constant and saturating concentrations of dCMP, dCDP or dCTP, irrespective of the enzyme tested (data not shown). PDTT0, PDTT1 and PDTT2 are still able to transfer deoxyribose 5-phosphate between bases, however, if the $K_m$ for dCMP is better than those measured for PDTM3, PDTM4 and PDTM5 (9.2 mM for PDTT0, 4.1 mM for PDTT1 and 6 mM for PDTT2), their catalytic efficiencies are not enhanced (Table 3).

TABLE 3

Kinetic parameters of PDT variants with an enlarge phosphate binding site in the presence of adenine as acceptor and deoxycytidine 5'-mono, -di and -triphosphate as donors of deoxyribose 5-phosphate.

| Enzymes[a] | Reaction[b] | $K_m$ dCMP mM[c] | $k_{cat}$ $s^{-1}$ | $k_{cat}/K_m$ $s^{-1} M^{-1}$ |
|---|---|---|---|---|
| PDTM3 | dCMP + A ⇌ dAMP + C | 22 | 0.3 | 13.6 |
| PDTM4 | dCMP + A ⇌ dAMP + C | 11 | 2.1 | 192 |
| PDTM5 | dCMP + A ⇌ dAMP + C | 12 | 1.99 | 166 |
| PDTT0 | dCMP + A ⇌ dAMP + C | 9.2 | 0.45 | 48.9 |
| PDTT1 | dCMP + A ⇌ dAMP + C | 4.1 | 0.46 | 112 |
| PDTT2 | dCMP + A ⇌ dAMP + C | 6 | 0.9 | 153 |
| PDTT1 | dCMP + A ⇌ dAMP + C | 8.9 | 0.08 | 8.9 |
| PDTT2 | dCMP + A ⇌ dAMP + C | 8.7 | 0.1 | 11.5 |
| PDTT1 | dCMP + A ⇌ dAMP + C | 5.5 | 0.5 | 103.7 |
| PDTT2 | dCMP + A ⇌ dAMP + C | 2 | 1.3 | 668.3 |

[a]PDT sequences are: PDTM3: R13 S92, PDTM4: R13 S92 S123, PDTM5: Q13 S92 S123, PDTT0: R13 G92 T93 S123, PDTT1: R13 G92 T93 S123 K157 and PDTT2: R13 Q91 G92 T93 S123 [b]same as above and [c]$V_{max}$ and $K_m$ were obtained from double reciprocal plots of initial velocity measurements. At least five different concentrations of dCMP, dCDP and dCTP were used. The $k_{cat}$ ($s^{-1}$) was calculated assuming a molecular mass of 108 kDa for each mutant In addition to their ability to transfer deoxyribose 5-phosphate, PDTT1 and PDTT2 also exchange deoxyribose 5-di and -triphosphate between bases. PDTT2 has the highest catalytic efficiency so far for both di- and tri-phosphorylated nucleotides. The improvement of deoxyribose triphosphate transferase of PDTT2 is mainly due to a better affinity for dCTP (2 mM) and a more efficient catalytic efficiency (668 $s^{-1} M^{-1}$).

The mutant enzyme Q13Q91S92S123 has been also tested. Briefly, 30 µg of this mutant has been mixed in 2 mM dAMP and 1 mM 5-FU in a final volume of 50 µL of MES buffer 50 mM pH6.0. 20 minutes later, 25% of 5-F-dUMP have been formed, demonstrating that this mutant has a significant phosphodesoxyribosyltransferase activity, especially on mono-Phosphate carrying nucleosides.

The catalytic activity of the mutant enzymes PDTT2, PDTT3, PDTT3b, PDTT4, PDTT5, PDTT6, PDTT7 has been compared. Briefly, a sufficient amount of enzyme mutant necessary to obtain a linear reaction over a period of one hour at 37° C. has been mixed in 2 mM dCTP and 1 mM Adenine in a final volume of 50 µL of MES buffer 50 mM pH6.0. Assays were incubated for 60 min at 37° C. The products of the reactions were analyzed each 7 min by Rapid resolution high performance liquid chromatography using a reverse-phase column (ZORBAX Eclipse XDB-C18 2.1*50 mm 1.804) with a flow rate of 0.25 ml/min and a linear gradient of 1-12% $CH_3CN$ (2-25% $CH_3CN$ or 1-90% $CH_3CN$) in 20 mM triethylammonium acetate, pH 7.5, buffer for 7 min. The results are indicated in Table 4.

TABLE 4 catalytic activities of PDTT2, PDTT3, PDTT3b, PDTT4, PDTT5, PDTT6, PDTT7 expressed in nmol of dATP formed/min/mg of enzyme protein.

| Enzymes | Reaction | Catalytic activity (nmol of dATP formed/min/mg of enzyme protein) |
|---|---|---|
| PDTT2 | dCTP + A ⇌ dATP + C | 9.6 |
| PDTT3 | dCTP + A ⇌ dATP + C | 2.7 |
| PDTT3b | dCTP + A ⇌ dATP + C | 6.5 |
| PDTT4 | dCTP + A ⇌ dATP + C | 10.4 |
| PDTT5 | dCTP + A ⇌ dATP + C | 27 |
| PDTT6 | dCTP + A ⇌ dATP + C | 18.6 |
| PDTT7 | dCTP + A ⇌ dATP + C | 17.9 |

Further, the cinetic parameters of these mutant enzymes were analysed, using a specific spectrophotometric assay. Briefly, the assay consists in measuring the formation of the final product (2,8 dihydroxyadenine) of the reaction:

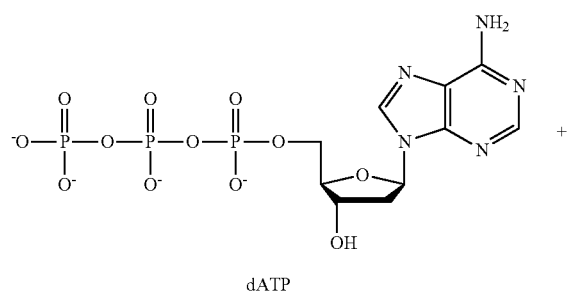
dATP

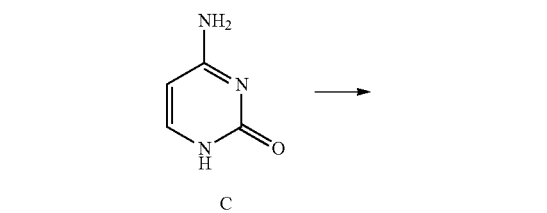
C

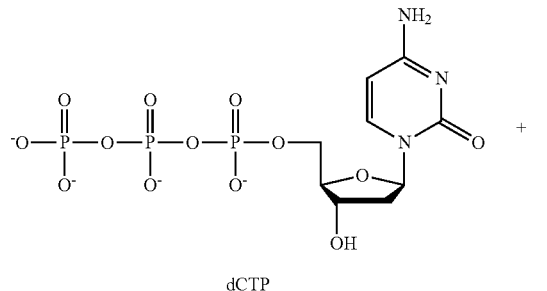
dCTP

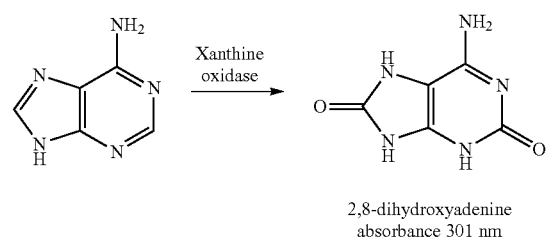
2,8-dihydroxyadenine
absorbance 301 nm

Briefly, the assay was performed using the coupling of two enzymes: the variant (PDTT2, PDTT4, PDTT5, PDTT6, or PDTT7) to be tested and xanthine oxidase (obtained from Roche). The reaction mixture contained varying concentrations of dATP, 1 mM cytosine in a 50 mM MES buffer pH6.0 at 37° C. The reaction was initiated by adding 30 units of the purified variant to be tested and xanthine oxidase (Roche). The released adenine was then oxidized in 2,8-dihydroxyadenine which absorbs at 301 nm. The formation (i.e. concentration) of 2,8 dihydroxyadenine was measured by spectrophotometry. The results are indicated in Table 5. They show that the four variants PDTT4, 5, 6 and 7 have a better affinity for dATP and a better catalytic efficiency ($k_{cat}/K_m$) than PDTT2.

| Enzymes | Reaction | $K_m$ dATP mM | $k_{cat}$ $s^{-1}$ | $k_{cat}/K_m$ $M^{-1}s^{-1}$ |
|---|---|---|---|---|
| PDTT2 | dATP + C ⇌ dCTP + A | 6.1 | 12.6 | $2 \cdot 10^3$ |
| PDTT3 | dATP + C ⇌ dCTP + A | | | |
| PDTT3b | dATP + C ⇌ dCTP + A | | | |
| PDTT4 | dATP + C ⇌ dCTP + A | 2.3 | 8.8 | $3.8 \cdot 10^3$ |
| PDTT5 | dATP + C ⇌ dCTP + A | 0.2 | 8.78 | $4.28 \cdot 10^4$ |
| PDTT6 | dATP + C ⇌ dCTP + A | 0.5 | 10 | $1.9 \cdot 10^4$ |
| PDTT7 | dATP + C ⇌ dCTP + A | 2.6 | 10 | $3.8 \cdot 10^3$ |

In Vitro Synthesis of Deoxynucleotide Analogues

Since NDT exhibits a broad specificity for the acceptor base, from substitutions on the heterocyclic part to non-pyrimidine rings, simplified purines or expanded guanine, enzymatic syntheses were conducted using the enzyme mutants PDTM4, PDTM5 and/or PDTT2, with different deoxynucleotides donors and bases as acceptors (see FIG. 2, and Table 4 below).

All the different variants, tested here were able to transfer deoxyribose 5-phosphate, deoxyribose 5-triphosphate or deoxyribose 5-1-thiotriphosphate between cytosine or adenine and analogs of natural bases such as 5-fluorouracil, 5-bromouracil, 2,6-diaminopurine, 6-chloropurine, and 2,6-dichloropurine. The efficiency of the transfer was dependent on the nature of the acceptor base and roughly followed that of NDT with its natural substrates (Kaminski P. A. et al, *J. Biol. Chem.* 2002).

TABLE 4

Specific activities of PTM4, PDTM5 and PDTT2 variants in the presence of different donors and nucleoside analogues as acceptors of deoxyribose 5-phosphate or deoxyribose 5-triphosphate.

| Reaction | Product | PDTM4 | PDTM5 | PDTT2 |
|---|---|---|---|---|
| dCMP + 5-BrU → C + 5-Br-dUMP | 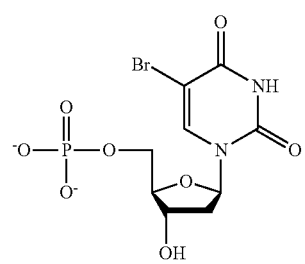 | 35 | 26 | 10.7 |

TABLE 4-continued

Specific activities of PTM4, PDTM5 and PDTT2 variants in the presence
of different donors and nucleoside analogues as acceptors of deoxyribose 5-phosphate or deoxyribose 5-triphosphate.

| Reaction | Product | PDTM4 | PDTM5 | PDTT2 |
|---|---|---|---|---|
| dAMP + 5-FU → A + 5-F-dUMP | | 43 | 47 | 48.4 |
| dCMP + 2,6-D → C + 2,6-DMP | | 96 | 78 | 95.8 |
| dCMP + 6-chloropurine → C + 6-chloropurine 2'-deoxyribose 5'-monophosphate | | 24 | 15 | 75 |
| dCMP + 2,6-chloropurine → C + 2,6-dichloropurine 2'-deoxyribose 5'-monophosphate | | 32 | 19 | 37 |
| dCTP + 5-BrU → C + 5-Br-dUTP | | | | 12 |
| dCTP + 5-FU → C + 5-F-dUTP | | | | 39.4 |

TABLE 4-continued

Specific activities of PTM4, PDTM5 and PDTT2 variants in the presence of different donors and nucleoside analogues as acceptors of deoxyribose 5-phosphate or deoxyribose 5-triphosphate.

| Reaction | Product | PDTM4 | PDTM5 | PDTT2 |
|---|---|---|---|---|
| dCTP + 2,6-D → C + 2,6-DTP | [structure of 2,6-diaminopurine 2'-deoxyribose 5'-triphosphate] | | | 17 |
| dCTP + 6-chloropurine → C + 6-chloropurine 2'-deoxyribose 5'-triphosphate | [structure of 6-chloropurine 2'-deoxyribose 5'-triphosphate] | | | 15 |
| dCTP + 2,6-chloropurine → C + 2,6-dichloropurine 2'-deoxyribose 5'-triphosphate | [structure of 2,6-dichloropurine 2'-deoxyribose 5'-triphosphate] | | | 14 |
| dCTPαS + A → C + dATPαS | [structure of dATPαS] | | | 54 |

The donor concentration was 3 mM and the acceptor 1 mM except for dCTP 2 mM 5-BrU 1 mM and dAMP 2 mM 5-FU 1 mM. Activities are expressed in nanomoles of deoxynucleotides synthesized per min per mg of protein.

In summary, the results mentioned above confirm that the nucleoside 2-deoxyribosyltransferases family now contains two novel sets of variants: those with slightly altered substrate specificity (i.e., only active on 2'-deoxynucleotide 5'-monophosphate such as PDTM4 or PDTM5) and those with a much broader specificity (PDTT1 and PDTT2). The latter have the unique property of transferring deoxyribose 5-mono, -di, -triphosphate and 1-thiotriphosphate between various nucleobases. This property is unlikely to exist in nature since nucleotide metabolic enzymes are highly specialized and recognize usually one particular substrate.

The utility of such enzymes is multiple: as tools for chemists to synthesize deoxynucleotides enzymatically; for geneticists to manipulate genomes by controlled mutagenesis; for synthetic biologists to incorporate unnatural deoxynucleotides in vitro and in vivo, thereby enabling the exploration of genotypic and phenotypic options so far unselected by natural evolution of nucleic acids.

BIBLIOGRAPHIC REFERENCES

Bao, J., and Ryu, D. D. (2007) Total biosynthesis of deoxynucleoside triphosphates using deoxynucleoside monophosphate kinases for PCR application. *Biotechnol Bioeng* 98, 1-11

Brinster et al., *Nature*, 296:39-42, 1982

Burgess, K., and Cook, D. (2000) Syntheses of nucleoside triphosphates. *Chem Rev* 100, 2047-2060

Caton-Williams, J., Smith, M., Carrasco, N., and Huang, Z. (2011) Protection-free one-pot synthesis of 2'-deoxynucleoside 5'-triphosphates and DNA polymerization. *Org Lett* 13, 4156-4159

Doddapaneni, K., Zahurancik, W., Haushalter, A., Yuan, C., Jackman, J., and Wu, Z. (2011) RCL hydrolyzes 2'-deoxyribonucleoside 5'-monophosphate via formation of a reaction intermediate. *Biochemistry* 50, 4712-4719

Eriksson, S., Munch-Petersen, B., Johansson, K., and Eklund, H. (2002) Structure and function of cellular deoxyribonucleoside kinases. *Cell Mol Life Sci* 59, 1327-1346

Freeman, G. A., Shaver, S. R., Rideout, J. L., and Short, S. A. (1995) 2-amino-9-(3-azido-2,3-dideoxy-beta-D-erythro-pentofuranosyl)-6-substitute d-9H-purines: synthesis and anti-HIV activity. *Bioorg Med Chem* 3, 447-458

Gerlt, J. A., and Babbitt, P. C. (2009) Enzyme (re)design: lessons from natural evolution and computation. *Curr Opin Chem Biol* 13, 10-18

Gibson, D. G., et al. (2010) Creation of a bacterial cell controlled by a chemically synthesized genome. *Science* 329, 52-56

Gibson, D. G., Smith, H. O., Hutchison, C. A., 3rd, Venter, J. C., and Merryman, C. (2010) Chemical synthesis of the mouse mitochondrial genome. *Nat Methods* 7, 901-903

Ghiorghi, Y. K., Zeller, K. I., Dang, C. V., and Kaminski, P. A. (2007) The c-Myc target gene Rcl (C6orf108) encodes a novel enzyme, deoxynucleoside 5'-monophosphate N-glycosidase. *J Biol Chem* 282, 8150-8156

Hebrard C., et al, *Cancer Gene Therapy* 2009, 16, 541-550

Johnson, D. C., 2nd, and Widlanski, T. S. (2004) Overview of the synthesis of nucleoside phosphates and polyphosphates. *Curr Protoc Nucleic Acid Chem Chapter* 13, Unit 13 11

Kaminski, P. A. (2002) Functional cloning, heterologous expression, and purification of two different N-deoxyribosyltransferases from *Lactobacillus helveticus. J Biol Chem* 277, 14400-14407

Kaminski, P. A., Dacher, P., Dugue, L., and Pochet, S. (2008) In vivo reshaping the catalytic site of nucleoside 2'-deoxyribosyltransferase for dideoxy- and didehydronucleosides via a single amino acid substitution. *J Biol Chem* 283, 20053-20059

Khakshoor, O., and Kool, E. T. (2011) Chemistry of nucleic acids: impacts in multiple fields. *Chem Commun* 47, 7018-7024

Ladner, W. E., and Whitesides, G. M. (1985) Enzymatic-Synthesis of Deoxy-Atp Using DNA as Starting Material. *J Org Chem* 50, 1076-1079

Mikhailopulo, I. A., and Miroshnikov, A. I. (2011) Biologically important nucleosides: modern trends in biotechnology and application. *Mendeleev Commun* 21, 57-68

Miller and Rosman, *BioTechniques,* 7:980-990, 1992

Nordlund, P., and Reichard, P. (2006) Ribonucleotide reductases. *Annu Rev Biochem* 75, 681-706

Porter, D. J., Merrill, B. M., and Short, S. A. (1995) Identification of the active site nucleophile in nucleoside 2-deoxyribosyltransferase as glutamic acid 98. *J Biol Chem* 270, 15551-15556

Warren, R. A. (1980) Modified bases in bacteriophage DNAs. *Annu Rev Microbiol* 34, 137-158

Yang, Y., Padilla, A., Zhang, C., Labesse, G., and Kaminski, P. A. (2009) Structural characterization of the mammalian deoxynucleotide N-hydrolase Rcl and its stabilizing interactions with two inhibitors. *J Mol Biol* 394, 435-447

The invention claimed is:

1. A mutant phosphodeoxyribosyltransferase enzyme comprising amino acid sequence SEQ ID NO:1, in which the Aspartic acid at position 92 is replaced by a Serine (S) or a Glycine (G), provided that, when the Aspartic acid at position 92 is replaced by a Glycine (G), the Valine amino acid at position 93 is replaced by a Threonine (T), or a Proline (P), or a Serine (S) or a Glycine (G).

2. The mutant enzyme of claim 1 comprising amino acid sequence SEQ ID NO:3 corresponding to SEQ ID NO:1 in which the amino acid at position 92 is replaced by a Serine (S).

3. The mutant enzyme of claim 1, further comprising at least one mutation selected from the group consisting of:
   (1) the Asparagine amino acid at position 123 is replaced by Serine (S);
   (2) the Phenylalanine amino acid at position 13 is replaced by an Arginine (R) or a Glutamine (Q);
   (3) the Glutamic acid at position 91 is replaced by a Glutamine (Q); and
   (4) the Tyrosine amino acid at position 157 is replaced by a Lysine (K) or an Arginine (R).

4. The mutant enzyme of claim 1 comprising amino acid sequence SEQ ID NO:4, corresponding to SEQ ID NO:1 in which the amino acid at position 92 is replaced by a Serine (S) and the amino acid at position 123 is replaced by a Serine (S).

5. The mutant enzyme of claim 1 comprising amino acid sequence SEQ ID NO:5, corresponding to SEQ ID NO:1 in which the amino acid at position 92 is replaced by a Serine (S) and the amino acid at position 13 is replaced by an Arginine (R).

6. The mutant enzyme of claim 1 comprising amino acid sequence SEQ ID NO:6, corresponding to SEQ ID NO:1 in which the amino acid at position 92 is replaced by a Serine (S), the amino acid at position 13 is replaced by an Arginine (R), and the amino acid at position 123 is replaced by a Serine (S).

7. The mutant enzyme of claim 1 comprising amino acid sequence SEQ ID NO:7, corresponding to SEQ ID NO:1 in which the amino acid at position 92 is replaced by a Serine (S), the amino acid at position 13 is replaced by a Glutamine (Q), and the amino acid at position 123 is replaced by a Serine (S).

8. The mutant enzyme of claim 1 comprising amino acid sequence SEQ ID NO:8, corresponding to SEQ ID NO:1 in which the amino acid at position 92 is replaced by a Glycine (G), the amino acid at position 13 is replaced by an Arginine (R), the amino acid at position 123 is replaced by a Serine (S), and the amino acid at position 93 is replaced by a Threonine (T).

9. The mutant enzyme of claim 1 comprising amino acid sequence SEQ ID NO:9 corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Threonine (T) and the amino acid at position 157 is replaced by a Lysine (K).

10. The mutant enzyme of claim 1 comprising amino acid sequence SEQ ID NO:10, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Threonine (T) and the amino acid at position 91 is replaced by a Glutamine (Q).

11. The mutant enzyme of claim 1 comprising amino acid sequence SEQ ID NO:35, corresponding to SEQ ID NO:1 in which the amino acid at position 92 is replaced by a Glycine (G), the amino acid at position 13 is replaced by a Glutamine (Q), the amino acid at position 123 is replaced by a Serine (S), the amino acid at position 93 is replaced by a Threonine (T) and the amino acid at position 157 is replaced by a Lysine (K).

12. The mutant enzyme of claim 1 comprising amino acid sequence SEQ ID NO:36, corresponding to SEQ ID NO:1 in which the amino acid at position 92 is replaced by a Serine (S), the amino acid at position 13 is replaced by a Glutamine (Q), the amino acid at position 123 is replaced by a Serine (S), the amino acid at position 91 is replaced by a Glutamine (Q) and the amino acid at position 157 is replaced by a Lysine (K).

13. The mutant enzyme of claim 1 comprising amino acid sequence SEQ ID NO:37, corresponding to SEQ ID NO:1 in which the amino acid at position 92 is replaced by a Glycine (G), the amino acid at position 13 is replaced by a Glutamine (Q), the amino acid at position 123 is replaced by a Serine (S), the amino acid at position 93 is replaced by a Threonine (T), the amino acid at position 91 is replaced by a Glutamine (Q) and the amino acid at position 157 is replaced by a Lysine (K).

14. The mutant enzyme of claim 1 comprising amino acid sequence SEQ ID NO:38, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Proline (P), the amino acid at position 91 is replaced by a Glutamine (Q,) and the amino acid at position 157 is replaced by a Lysine (K).

15. The mutant enzyme of claim 1 comprising amino acid sequence SEQ ID NO:39, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Glycine (G), the amino acid at position 91 is replaced by a Glutamine (Q,) and the amino acid at position 157 is replaced by a Lysine (K).

16. The mutant enzyme of claim 1 comprising amino acid sequence SEQ ID NO:40, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Serine (S), the amino acid at position 91 is replaced by a Glutamine (Q,) and the amino acid at position 157 is replaced by a Lysine (K).

17. The mutant enzyme of claim 1 comprising amino acid sequence SEQ ID NO:41, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Proline (P), the amino acid at position 91 is replaced by a Glutamine (Q,) and the amino acid at position 157 is replaced by an Arginine (R).

18. The mutant enzyme of claim 1 comprising amino acid sequence SEQ ID NO:42, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Glycine (G), the amino acid at position 91 is replaced by a Glutamine (Q,) and the amino acid at position 157 is replaced by an Arginine (R).

19. The mutant enzyme of claim 1 comprising amino acid sequence SEQ ID NO:43, corresponding to SEQ ID NO:1 in which the amino acid at position 92 is replaced by a Glycine (G), the amino acid at position 13 is replaced by an Arginine (R), the amino acid at position 123 is replaced by a Serine (S), the amino acid at position 93 is replaced by a Serine (S), the amino acid at position 91 is replaced by a Glutamine (Q) and the amino acid at position 157 is replaced by an Arginine (R).

20. A polynucleotide encoding the mutant enzyme of claim 1 having one of the nucleotide sequences of SEQ ID NO: 24 to 31 or of SEQ ID NO: 44 to 49.

21. A recombinant vector comprising the polynucleotide of claim 20.

22. A non-human recombinant cell containing the polynucleotide of claim 20 or the recombinant vector of claim 21.

23. A method for producing a mutant enzyme of claim 1, said method comprising the steps of:
a) culturing the recombinant cell of claim 22 in appropriate conditions so as to allow the production of the protein(s) encoded by the recombinant vector contained in said recombinant cell,
b) collecting the mutant enzyme which is expressed from the cell culture.

24. A kit containing:
at least one mutant enzyme of claim 1,
a polynucleotide of claim 20, or
a recombinant vector of claim 21.

* * * * *

UNITED STATES PATENT AND TRADEMARK OFFICE
CERTIFICATE OF CORRECTION

PATENT NO. : 9,523,084 B2  
APPLICATION NO. : 14/441560  
DATED : December 20, 2016  
INVENTOR(S) : Pierre-Alexandre Kaminski et al.

Page 1 of 1

It is certified that error appears in the above-identified patent and that said Letters Patent is hereby corrected as shown below:

In the Specification

Column 23, Line 37:
Please delete "dCTPaS" and insert --dCTPαS--

Column 25, Line 4:
Please delete "DH5a" and insert --DH5α--

Column 25, Line 29:
Please delete "2 ml min'" and insert --2 ml min$^{-1}$--

Column 30, Table 3, Line 11:
Please delete "dCMP + A ⇄ dAMP + C" and insert -- dCDP + A ⇄ dADP + C--

Column 30, Table 3, Line 12:
Please delete "dCMP + A ⇄ dAMP + C" and insert --dCDP + A ⇄ dADP + C --

Column 30, Table 3, Line 13:
Please delete "dCMP + A ⇄ dAMP + C" and insert --dCTP + A ⇄ dATP + C --

Column 30, Table 3, Line 14:
Please delete "dCMP + A ⇄ dAMP + C" and insert --dCTP + A ⇄ dATP + C--

Column 30, Line 46:
Please delete "1.804" and insert --1.8μM--

Signed and Sealed this
Second Day of January, 2018

Joseph Matal
*Performing the Functions and Duties of the*
*Under Secretary of Commerce for Intellectual Property and*
*Director of the United States Patent and Trademark Office*